United States Patent [19]

Stossel et al.

[11] Patent Number: 5,576,213
[45] Date of Patent: Nov. 19, 1996

[54] PRESERVATION OF BLOOD PLATELETS

[75] Inventors: Thomas P. Stossel, Belmont; John H. Hartwig, Jamaica Plain; Paul A. Janmey, Arlington, all of Mass.

[73] Assignee: Brigham & Women's Hospital, Inc., Boston, Mass.

[21] Appl. No.: 279,226

[22] Filed: Jul. 22, 1994

Related U.S. Application Data

[62] Division of Ser. No. 19,045, Feb. 18, 1993, Pat. No. 5,358,844.

[51] Int. Cl.$^6$ ............................................. G01N 33/49
[52] U.S. Cl. .............................. 436/18; 436/8; 435/2; 424/532
[58] Field of Search ............................. 436/18, 8, 17; 435/4, 2; 424/529, 532

[56] References Cited

U.S. PATENT DOCUMENTS

| | | | |
|---|---|---|---|
| 3,890,435 | 6/1975 | Broadbent et al. | 424/115 |
| 4,412,835 | 11/1983 | Spencer | 604/29 |
| 4,603,209 | 7/1986 | Tsien et al. | 548/236 |
| 5,071,741 | 12/1991 | Brockbank | 435/1 |
| 5,114,847 | 5/1992 | Jungfer et al. | 435/41 |
| 5,185,160 | 2/1993 | Chao | 424/532 |
| 5,190,880 | 3/1993 | Cassou et al. | 435/296 |
| 5,234,808 | 8/1993 | Murphy | 435/2 |

FOREIGN PATENT DOCUMENTS

0297946A2  4/1989  European Pat. Off. .

OTHER PUBLICATIONS

Cohen et al, Platelet Preservation, vol. 273, No. 16, "Comparison of Radioactivity Yields of Platelet Concentrates Derived from Blood Anticoagulated with EDTA and ACD".

Gottschall et al, Transfusion, vol. 26, No. 5 (1986) "Studies of the minimum temperature at which human platelets can be stored with full maintenance of viability".

Remington's Pharmaceutical Sciences, Gennaro et al, Philadelphia College of Pharmacy and Science, (1990), pp. 800–803.

Principles of Transfusion Medicine, Rossi, et al, Williams & Wilkins (1991), pp. 205–207, 212.

Blood Transfusion in Clinical Medicine, Mollison et al, Blackwell Scientific Publications, (1993), p. 642.

Hematology (Fourth Edition), Williams et al, McGraw-Hill Publishing Company, (1990), pp. 368–377 and 1233–1250.

Hematology, Basic Principles and Practice, Hoffman et al, Churchill Livingstone, (1991), pp. 1176–1197.

Physical Chemistry, Atkins, P. W., W. H. Freeman and Company, San Francisco, CA, (1982), p. 935.

Cassimeris, L. et al., J. Cell Biol. 110:1067–1075, "Chemoattractant–stimulated Polymorphonuclear Leukocytes Contain Two Populations of Actin Filaments that Differ in Their Spatial Distributions and Relative Stabilities".

McManus, M. J. et al., Am. J. Physiol. 265:C562–570 (1993), "Laser light–scattering system for studying cell volume regulation and membrane transport processes".

Hartwig, J., 1992 J. Cell Biology 118 (6): 1421–1442), "Mechanisms of Actin Rearrangements Mediating Platelet Activation".

Hartwig, J. and DeSisto, M., 1991 J. Cell Biol. 112:407–425. "The Cytoskeleton of the Resting Human Blood Platelet: Structure of the Membrane Skeleton and its Attachment to Actin Filaments".

(List continued on next page.)

Primary Examiner—James C. Housel
Assistant Examiner—Rachel Heather Freed
Attorney, Agent, or Firm—Wolf, Greenfield and Sacks, P.C.

[57] ABSTRACT

Methods and compositions for preserving platelets at cryogenic temperatures with retention of hemostatic activity are provided. The compositions include a first agent for inhibiting actin filament severing and a second agent for inhibiting actin polymerization. Contacting the platelets with the first and second agents prior to exposure to cold temperature prevents cold-induced platelet activation.

7 Claims, 6 Drawing Sheets

OTHER PUBLICATIONS

Yin, H. L., 1987 BioEssays 7:176–179, "Gelsolin: Calcium—and Polyphosphoinositide–Regulated Actin–Modulating Protein".

Stossel, T., 1989 J. Biol. Chem. 264:18261–18264. "From Signal to Pseudopod—How Cells Control Cytoplasmic Actin Assembly".

Janmey, P. A., et al., 1985 Biochemistry 24:3714–3723. "Interactions of Gelsolin and Gelsolin–Actin Complexes with Actin Efects of Calcium on Actin Nucleation, Filament Severing, and End Blocking".

Davies, T. D., et al., 1989 J. Biol. Chem. 264:19600–19606, "Cyto-plasmic $Ca^{2+}$ Is Necessary for Thrombin–induced Platelet Activation".

Cobbold, P. and Rink, T., 1987 Biochem. J. 248:313–328. "Fluorescence and bioluminescence measurement of cytoplasmic free calcium".

R. Haugland, Handbook of Fluorescent Probes and Research Chemicals, 5th Edition, 1992–1994.

White, J. B. and Krivit, W., 1967 Blood 30:625–635. "An Ultra-structural Basis for the Shape Changes Induced in Platelets By Chilling".

White, J. G., 1982 Am. J. Path. 108:184–195, "Influence of Taxol on the Responses of Platelets to Chilling".

Schliwa, M., 1982 J. Cell. Biol. 92:79–91. Action of Cytochalasin D on Cytoskeletal Networks.

Mooseker, M. S., 1986 J. Cell Biol. 102:282–288. "Cytochalasin B Slows But Does Not Prevent Monomer Addition at the Barbed End of the Actin Filament".

Lin et al., 1980 J. Cell. Biol. 84:455–460. Cytochalasins Inhibit Nuclei–Induced Actin Polymerization By Blocking Filament Elongation.

Ohmori, H., et al., 1992, J. Cell Biol. 116(4):933–941. Direct Proof That the Primary Site of Action of Cytochalasin on Cell Motility Processes Is Actin.

Cooper, J. A., 1987 J. Cell Biol. 105:1473–1478. Effects of Cytochalasin and Phalloidin on Actin.

Spector, I., et al., 1989 Cell Motility and the Cytoskelton 13:127–144. Latrunculins–Novel Marine Macrolides That Disrupt Microfilament Organization and Affect Cell Growth: 1. Comparison With Cytochalasin D.

Bennett, J. S. and Shattil, S. J., 1990, "Platelet function," Hematology, Williams, W. J., et al., Eds. McGraw Hill, pp. 1233–1250.

Slichter, S. J., 1981 Vox Sang 40 (Suppl 1), pp. 72–86, Clinicial Testing and Laboratory–Clinical Correlations Murphy, P. H. and Gardener F. H., 1969 N. Engl. J. Med. 280:1094–1098. "Platelet Preservation—Effect of Storage Temperature on Maintenance of Platelet Viability—Deleterious . . . Storage".

Handin, R. I. and Valeri, C. R., 1971 N. Engl. Med. 285:538–543. "Hemostatic Effectiveness of Platelets Stored at 22° C.".

Tsien, R., et al., (1982) J. Cell. Biol. 94:325–334. Calcium Homeostasis in Intact Lymphocytes: Cytoplasmic Free Calcium Monitored With a New, Intracellularly Trapped Fluorescent Indicator.

Janmey, P. and Stossel, T., 1987 Nature 325:362–364. Modulation of Gelsolin function by Phosphatidylinositol 4,5–bisphosphate.

Janmey, P., et al., 1987 J. Biol. Chem. 262:1228–1232. "Polyphoinositide Micelles and Polyphosphoinositide-–containing Vesicles . . . of Actin Filaments Blocked by Gelsolin".

Tsuyruo, et al., 1986 Biochem. Pharmacol. 35:1087–1090, "Effects of Cytochalasins and Colchicine on the Accumulation and Retention of Daunomycin and Vincristine in Drug Resistant Tumor Cells".

Lipski, K. et al. 1987 Anal. Biochem. 161:332–340, Cytochalasin B Preparation, Analysis in Tissue Extracts, and Pharmacokinetics after Intraperitonea Bolus Administration in Mice.

Janmey, P. A., and Stossel, T., 1989 J. Biol. Chem., 264:4825–4831 "Gelsolin–Polyphosphoinositide Interaction".

Janmey, P. A. et al., 1992 J. Biol. Chem. 267:11818–11823. "Phosphoinositide–binding Peptides Derived from the Sequences of Gelsolin and Villin".

Kwiatkowski, O. J., et al., 1989 J. Cell. Biol. 108:1717–1726. Identification of Critical Functional and Regulatory Domains in Gelsolin.

Way, et al. 1989 J. Cell. Viol. 109:593–605, "Expression of Human Plasma Gelsolin in *Escherichia coli* and Dissection of Actin Binding Sites by Segmental Deletion Mutagenesis".

Hartwig, J. H. and Kwiatkowski, O. J., 1991 Curr. Opin Cell Biol. 3:87–97, Actin–binding proteins.

Vanderkerhove, J. and Vancompernolle, K., 1992 Curr. Opion Cell. Biol. 4:36–42, Structural relationships of actin–binding proteins.

Aktories, K. and Wegner, A., 1989 J. Cell Biol. 109:1385. ADP–ribosylation of Actin by Clostridial Toxins.

Hartwig, J. and Janmey, P. 1989 Biochim. Biophys. Acta 1010:64–71 Stimulation of a calcium–dependent actin nucleation activity by phorbol 12–myristate 13–acetate in rabbit macrophage cytoskeletons.

Hartwig, J., et al. 1989 J. Cell Biol. 109:1571–1579, Association of Profilin with Filament–free Regions of Human Leukocyte and Platelet Membranes and Reversible Membrane Binding during Platelet Activation.

Casella, J., et al, 1981 Nature (Lond.) 293:302–305, "Cytochalasin D inhibits actin polymerization and induces depolymerization of actin filaments formed during platelet shape change".

Fox, J. and D. Phillips, 1981 Nature (Lond.) 292:650–652, "Inhibition of actin polymerization in blood platelets by cytochalasins".

Schliwa, M., et al., 1981 Proc. Natl. Acad. Sci. USA 78:4329–4333, 5417–5420, Stabilization of the cytoplasmic ground substance in detergent–opened cells and a structural and biochemical analysis of its comosition.

Howard, T. H. and Oresajo, J., 1987 Cell Motility and the Cytoskeleton 5:545–557, "A Method for Quantifying F–Actin in Chemotactic Peptide Activated Neutrophils: Study of the Effect of of tBOC Peptide".

Zucker, M. B. and Borrelli, J., 1954 Blood 9:602, "Reversible terations in Platelet Morphology Produced by Anticoagulants and by Cold".

Handin, R. I. et al., 1970 Transfusion 10:305, Platelet Response to Hypotonic Stress after Storage at 4 C or 22 C.

Tsien, R., 1980 Biochemistry 19:2396–2404, "New Calcium Indicators and Buffers with High Selectivity against Magnesium and Protons . . . ".

Rinder et al., Blood Cells (1992) 18:445–456, "Activation of platelet Concentration During Preparation and Storage".

Bousquet et al., Cancer Research 60, 1431–1439, Mar. 1990, "Effects of Cytochalasin B in Culture and in Vivo on Murine Madison 109 Lung Carcinoma and on B16 Melanoma".

Faulstich et al., Biochemistry 1980, 3334–3343, "Virotoxins: Actin–Binding Cyclic Peptides of Amanita virosa Mushrooms".

P. Chardin et al, The EMBO Journal, vol. 8, No. 4, pp. 1087–1092, "The mammalian G Protein rhoC is ADP–ribosylated by Clostridium botulinum exoenzyme C3 and affects actin microfilaments in Vero cells".

T. Wieland et al., 1980 American Chemical Society, vol. 19, No. 4 pp. 3363–3367, "Concentration–Dependent Influence of Various Cytochalasins and Chaetoglobosins on the Phalloidin–Induced Polymerization of G–Actin in 0.6 M Potassium Iodide".

I. Yahara et al., The Journal of Cell Biology, vol. 92, 1982, pp. 69–78, "Correlation between Effects of 24 Different Cytochalasins on Cellular Structures and Cellular Events and Those on Actin In Vitro".

Feinberg et al. Acc# 109:126490 CA.

Watts et al. Acc# 106:3344 CA.

Chignard et al. "Direct Evidence for the existence of . . . " Proc. Natl. Acad. Sci. USA vol. 83 pp. 8609–8613 Nov. 1986 Cell Biology.

Smith et al. "Facile Plalelet Adhesion to . . . " J. of Cell. Biochem. 47:54–61, 1991.

Oda et al. "Heterogeneity in Filamentous Actin . . . " Blood, vol. 79, No. 4, Feb. 15, 1992, 920–927.

Hartwig, "Mechanisms of Actin Rearrangements . . . " The J. of Cell Bio. vol. 118, No. 6, Sep. 1992, 1421–1442.

PRESERVATION OF BLOOD PLATELETS

This work funded by a government grant from the U.S. Public Health Service National Institute of Health, grant numbers HL19429 and HL47874.

This application is a division of application Ser. No. 08/019,045 filed Feb. 18, 1993, now U.S. Pat. No. 5,358,844.

FIELD OF THE INVENTION

This invention relates to methods and compositions for preserving platelets at cryogenic temperatures with retention of hemostatic activity. The methods involve the use of agents for inhibiting actin filament severing and agents for inhibiting actin polymerization.

BACKGROUND OF THE INVENTION

The absence of adequate numbers of hemostatically active blood platelets is associated with many disease states, some of which can only be treated by transfusion of blood products containing large numbers of viable platelets. Freshly obtained blood platelets mediate hemostasis by converting, where properly instructed, from discs to spiny pleated spheres that attach to breaks in blood vessels and to other platelets. This process, referred to as platelet activation, is triggered by a variety of different agonists, including thrombin, adenosine diphosphate (ADP), thromboxanes, collagen, von Willebrand's factor, as well as upon contact of platelets with glass.

Current practice permits platelets to be stored no longer than several days, after which the platelets are no longer hemostatically active and are discarded as "outdated". It is estimated that about 15% of procured units of blood are discarded as outdated. As a result of the short platelet shelf life, a large supply of donated blood is required to sustain each patient requiring platelet replacement therapy.

Given the problems of platelet availability, various attempts have been made to preserve platelets for longer periods of time with retention of hemostatic activity. Most of this work was done in the 1960's and early 1970's and culminated in the practice of room temperature storage. These studies revealed that while room temperature storage led rapidly to significant reduction in hemostatic function, the phenomenon of cold-induced platelet activation had more deleterious effects (Murphy, P. H. and Gardener, F. H., 1969 N. Engl. J. Med. 280:1094–1098; Handin, R. I. and Valeri, C. R., 1973 J. Engl. J. Med. 285:538–543). More recently, research has focused on the odification of platelet storage packs or bags to increase porosity and gas exchange, on nutrients, metabolites, pH and protease inhibitors (e.g., Murphy, S. et al., 1982 Blood 60:194–200; Rinder, H. M. and Snyder, E. L., 1992 Blood Cells 18:445–456). Because storage at non-refrigerated temperatures has been associated with microbial contamination of transfused platelets (Bennett, J. V., 1971 N. Engl. J. Med. 285:457–458; Buckholz, D. H., et al., 1971 N. Engl. J. Med. 285:429–433; Morrow, J. F., et al., 1991 JAMA 266:555–558) the Food and Drug Administration (FDA) limits platelet storage to five days.

To date, effort s to store platelets at reduced temperatures have proven unsuccessful because of the morphological changes which platelets undergo in response to cold temperatures. These changes, collectively referre to as "cold-induced platelet activation", result in substantially impaired hemostatic, function. In contrast to freshly obtained platelets, platelets that have been rewarmed following cold-induced activation share many structural features with glass-activated platelets but have substantially impaired hemostatic activity. Thus, although (agonist- or glass-induced) platelet activation and cold-induced platelet activation have in common some structural similarities, these activation processes yield quite distinctive functional results. To understand the processes which comprise agonist- and/or cold-induced activation and the differences between the two types of activation, the cytoskeletal structure of the resting platelet must first be considered.

Prior to activation, the resting platelet contains a highly organized cytoskeletal structure, with actin representing about a fifth of the total protein (Hartwig, J., 1992 J. Cell Biology 118(6):1421–1442). bout half of the actin in resting platelets is present as actin monomer ("G-actin") and is stored as a 1:1 complex with beta 4-thymosin or profilin. The remainder of the actin in resting platelets is organized into long filaments ("F-actin") which radiate outwardly from the platelet center. The filaments have a fast-growing end, the "barbed end", to which the actin monomers are added in a process alternatively referred to as actin assembly or actin polymerization.

Spontaneous actin assembly from monomers in vitro proceeds through a thermodynamically unfavorable nucleation step that limits the initial rate of this polymerization reaction. In vivo, various proteins regulate platelet activation by association with actin monomers and/or filaments. The presence in platelets of nearly stoichiometric quantities of actin monomer binding proteins, e.g. profilin and beta 4-thymosin, with affinities for actin monomer in the micromolar range, presumably p events spontaneous nucleation in vivo (Safer, D., et al., 1991 J. Biol. Chem. 266:4029–4032; Weeds, A. G., et al., 1992 Biochem. Soc. Trans. 19:1016–1020). By associating with actin monomers, these "sequestering proteins" render the monomers incapable of adding to the free pointed ends of actin filaments and less capable of adding to the (uncapped) barbed ends of actin filaments.

The exact interplay of these regulatory proteins with actin monomers and filaments and their involvement in platelet activation is not precisely understood. In the resting platelet, actin filaments bind via actin-binding proteins ("abp") to a dense spectrin-rich shell that laminates the plasma membrane (see e.g., Hartwig, J. and DeSisto, M., 1991 J. Cell Biol. 112:407–425). We have observed that upon stimulation by an agonist, such as thrombin, the resting platelet swells, presumably as a result of actin filament severing (see Hartwig, J., 1992 supra.). It is known that severing requires an increase in the intracellular free calcium concentration (Hartwig, J. and Yin, H. L., 1987 BioEssays 7:176–179).

Exposure of platelets to thrombin increases the intracellular calcium concentration to near micromolar levels in the absence of external calcium and to greater than micromolar levels when calcium is a component of the surrounding medium (see e.g., Oda, A., et al., 1991 Am. J. Physiol. 260:C242–C248). Calcium at micromolar levels leads to the formation of gelsolin-actin complexes in vitro (stossel, T., 1989 J. Biol. Chem. 264:18261–18264). In the resting platelet, >95% of the gelsolin is free, i.e., not complexed to actin (Lind, et al., 1987 J. Cell Biol. 105:833–842). Free gelsolin (not gelsolin-actin complexes) reportedly plays a role in calcium-dependent actin filament severing (Janmey, P. A., et al., 1985 Biochemistry 24:3714–3723). Loading cells with permeant calcium chelators reportedly quenches the increase in intracellular calcium concentration in response to agonists such as thrombin (Davies, T. D., et al., 1989 J. Biol. Chem. 264:19600–19606).

Various intracellular calcium chelating agents have been used as research tools to elucidate the role of calcium in platelet activation. These include derivatives and analogues of the calcium chelator BAPTA developed by Tsien et al., (see e.g., U.S. Pat. No. 4,603,209). Many of these chelators exhibit an increase in fluorescence emission (in response to appropriate excitation) upon binding free calcium. However, to be useful as intracellular chelating agents, these calcium chelators had to be derivatized with lipophilic groups, i.e., to render the chelators capable of penetrating the platelet membrane and entering the cytosol. Such intracellular calcium chelators have been used to measure intracellular calcium concentrations in human blood platelets at rest and during activation (Cobbold, P. and Rink, T., 1987 *Biochem. J.* 248:313–328). Very low intracellular calcium concentrations were achieved when large amounts of the chelators were loaded into the cytosol in the absence of an exogenous source of free (unchelated) calcium (Cobbold and Rink, 1987, supra.).

Platelet activation is manifested by transformation of the resting platelet (2) into a compact sphere (activated platelet, 10) from which extend spines (Filopodia, 4) and veils ("lamellipodial networks") (FIGS. 1 and 2). The filopodia comprise bundles of actin filaments ("filopodial bundles"). The veils contain shorter actin filaments (8) and represent a second type of filament organization. The generation of both of these actin structures requires gelsolin. We believe that removal of gelsolin from the core actin network, i.e., the population of actin filaments deep within the platelet, leads to formation of the filopodial bundles and that removal of gelsolin from severed actin filaments leads to formation of the lamellipodial network.

Much of what is known about the structural changes accompanying platelet activation has been learned from studying the barbed end actin polymerization activity of detergent-demembranated platelets in various states of activation. Barbed end actin polymerization activity is determined by observing the rate at which newly added actin monomer is incorporated into platelet filaments (see e.g., Hartwig, J. and Janmey, P., 1989 *Biochim. Biophys. Acta.* 3030:64–71). Because cytochalasin B is a well known inhibitor of a tin assembly onto the barbed ends of actin filaments, the existence and extent of barbed end activity is determined by observing the effect of cytochalasin B on the rate at which actin monomers are added to the barbed ends of actin filaments.

The cytochalasins and the related chaetoglobosins constitute a class of more than 24 structurally and functionally related mold metabolites. Several publications have reported that cytochalasin B prevents some of the platelet shape changes associated with cold-induced activation, but that other changes, e.g., distortions of intracellular membranes, were not prevented (White, J. B. and Krivit, W., 1967 *Blood* 30:625; White, J. G., 1982 *Am. J. Path.* 108:184). More recently, the cytochalasins have been reported to alter actin-based cytoskeletal morphology ( see e.g. , schliwa, M., 1982 *J. Cell Biol.* 92:79–91) and inhibit actin polymerization (see e.g., Mooseker, M. S., 1986 *J. Cell Biol.* 102:282–288).

In vitro studies using purified actin indicate that cytochalasins bind to the barbed end of actin filaments and inhibit its polymerization (see e.g., Linet al., 1980 *J. Cell Biol.* 84:455–460) by reducing the rate of monomer addition to the barbed end of growing filaments (see e.g., Ohmori, H., et al., 1992, *J. Cell Biol.* 116(4):933–941 and references cited therein). Although the detailed mechanism by which the cytochalasins inhibit actin polymerization has not been elucidated (e.g., Cooper, J. A., 1987 *J. Cell Biol.* 105:1473–1478), it is believed that the cytochalasins and related compounds interfere with the dynamic equilibrium that exists in nonmuscle cells between actin filaments (F-actin) and monomeric actin (G-actin) (see e.g., Spector, I., et al., 1989 *Cell Motility and the Cytoskeleton* 13:127–144 and references cited therein).

The above-cited references disclose the use of agents such as cytochalasin B and intracellular calcium chelators for characterizing the biochemical and morphological changes that occur during agonist- and/or glass-induced platelet activation. However, none of the cited references disclose the use of such agents, alone or in combination, for modulating or preventing cold-induced platelet activation. Accordingly, there is still a need for methods and pharmaceutical compositions to preserve platelets. In particular, there is still a need for methods for preserving platelets at cryopreservation temperatures, which methods preven cold-induced platelet activation. Such methods would permit the preservation of blood platelets with preserved hemostatic activity or longer periods of time than are currently possible.

SUMMARY OF THE INVENTION

The present invention provides methods and compositions for the cryopreservation of platelets with preserved hemos tatic activity. Also provided are methods for making a pharmaceutical composition containing the cryop reserved platelets and for administering the pharmaceutical composition to a mammal to mediate hemostasis. The methods are based upon the recognitio by Applicants that two processes, actin filament sever ing and actin polymerization, are essential pathways involved in cold-induced platelet activation and the concomitant loss of hemostatic function.

According to one aspect of the invention, a method for the cryopreservation of platelets with preserved hemostatic activity is provided. The method comprises contacting a preparation of platelets with a first agent for inhibiting actin filament severing and with a second agent or inhibiting actin polymerization to form a treated platelet preparation and storing the treated platelet preparation at a cryopreservation temperature. The platelets are collected from peripheral blood by standard techniques known to those of ordinary skill in the art. In a preferred embodiment the platelets are contained in a pharmaceutically-acceptable carrier prior to treatment with the first and second agents.

As used herein, actin filament severing refers to disruption of the non-covalent crosslinks between actin filaments and between filaments and the spectrin-rich shell that laminates the plasma membrane (FIG. 1). Severing requires an increase in the concentration of intracellular calcium. Accordingly, in a preferred embodiment, the first agent is an intracellular calcium chelator that is capable of penetrating the platalet membrane.

As used herein, actin polymerization refers to the process by which actin monomers ("G-actin") are assembled onto the fast-growing ("barbed end") of actin filaments ("F-actin"). Exemplary second agents for inhibiting actin polymerization include a class of fungal metabolites known as the cytochalasins. It is believed that the cytochalasins inhibit actin polymerization by constitutively mimicking the actions of endogenous, metabolically regulated barbed end capping agents, e.g. gelsolin, thereby reducing the rate of monomer addition onto the barbed end of growing filaments.

Following contact with the first and second agents, the treated platelets are stored at a cryopreservation temperature. As used herein, "cryopreservation temperature" refers to a temperature that is less than about 22° C. In a preferred embodiment, the cryopreservation temperature is less than about 15° C. In a most preferred embodiment, the cryopreservation temperature ranges from between about 0° C. to about 4° C.

According to an further aspect of the invention, a method for making a pharmaceutical preparation for administration to a mammal is provided. The method comprises preparing the above-described cryopreserved platelet preparation warming the platelet preparation, and neutralizing the first and second agents. If the treated platelets are not already contained in a pharmaceutically acceptable carrier, they are placed in a pharmaceutically-acceptable carrier prior to administration to the mammal. As used herein, the terms "neutralize" or "neutralization" refer to the process by which the first and second agents are rendered substantially incapable of further acting in the platelet preparation as agent for inhibiting actin filament severing and inhibiting actin polymerization, respectively.

According to yet another aspect of the invention, a method for mediating hemostasis in a mammal is provided. The method comprises administering the above-described pharmaceutical preparation to the mammal.

According to still another aspect of the invention, storage compositions and pharmaceutical compositions for mediating hemostasis are provided.

In one embodiment, the compositions comprise a pharmaceutically acceptable carrier, a plurality of platelets, a plurality of a first agent for inhibiting actin filament severing and a plurality of a second agent for inhibiting actin polymerization. In a storage composition, the first and second agents are present in the composition in sufficient amounts so as to prevent cold-induced platelet activation. As used herein, the phrase "cold-induced platelet activation" refers to the molecular and morphological changes that blood platelets undergo following exposure to cold temperatures, e.g., 4° C. In a pharmaceutical composition, the agents have been neutralized and the composition comprises a pharmaceutically acceptable carrier and a plurality of cryopreserved platelets having preserved platelet hemostatic activity.

In yet another embodiment, the pharmaceutical composition comprises a plurality of platelets, a plurality of a non-naturally occurring intracellular calcium chelator, a plurality of a non-naturally occurring second agent for inhibiting actin filament severing and a pharmaceutically acceptable carrier. Exemplary non-naturally occurring calcium chelators include the acetoxymethyl (AM) esters of the BAPTA family of calcium chelators (described below), and derivatives thereof. In a preferred embodiment, the calcium chelator is the acetoxymethyl derivative of quin-2 and the agent for inhibiting actin polymerization is cytochalasin B.

According to yet another aspect of the invention, a composition for preventing cold-induced platelet activation is provided. The composition includes a plurality of a first agent for inhibiting actin filament severing and a plurality of a second agent for inhibiting actin polymerization. The first and second agents are present in the composition in sufficient amounts sO as to prevent cold-induced platelet activation.

These and other aspects of the invention as well as various advantages and utilities will be more apparent with reference to the detailed description of the preferred embodiments and in the accompanying drawings.

DETAILED DESCRIPTION OF THE INVENTION

Figure 1:
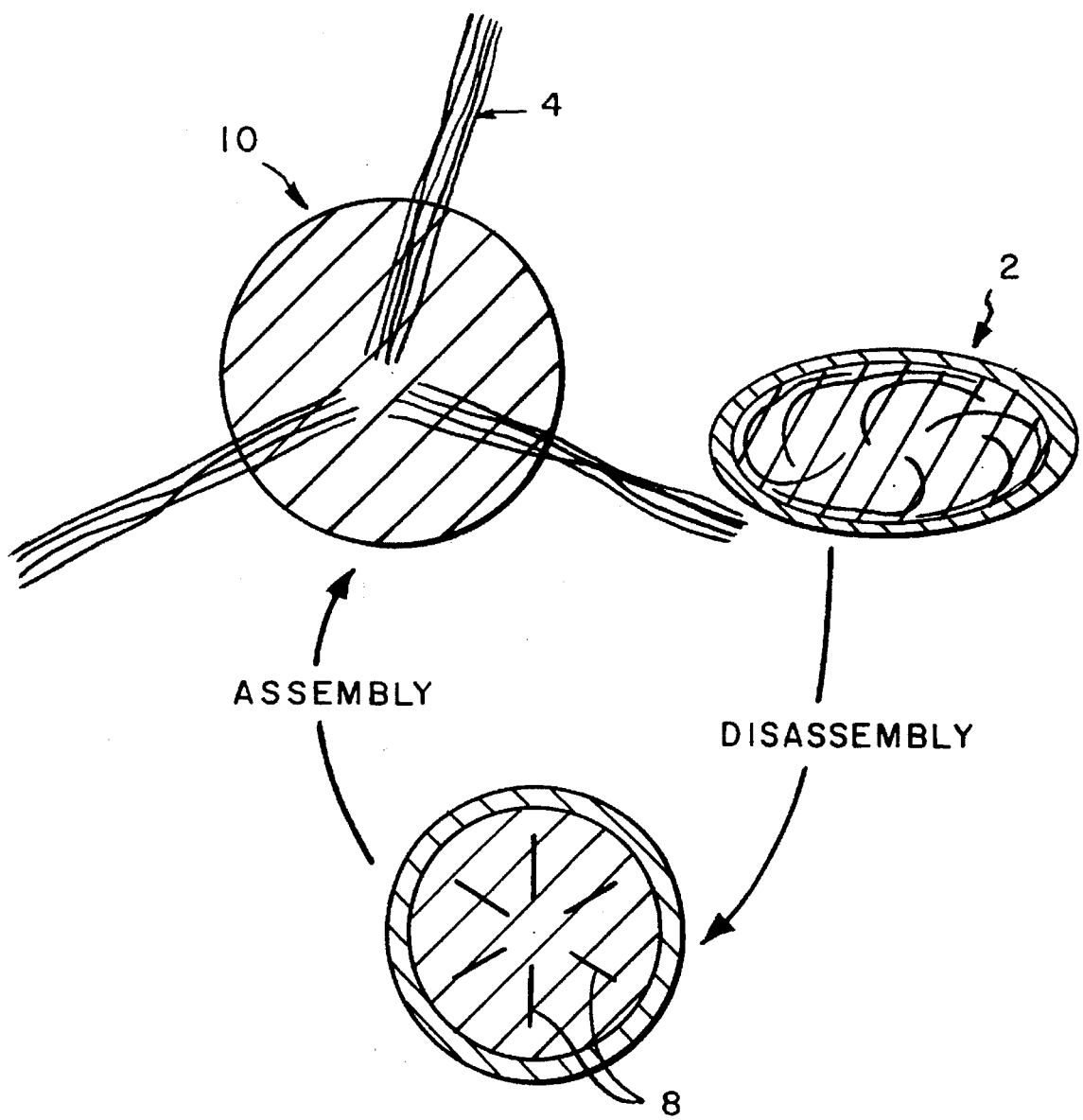
FIG. 1 schematically illustrates actin remodeling during platelet activation.

The instant invention embraces methods for preserving platelets with preserved hemostatic activity, storage compositions for preventing cold-induced platelet activation and pharmaceutical compositions for mediating hemostasis.

The compositions comprise a pharmaceutically acceptable carrier, a plurality of platelets, a plurality of a first agent for inhibiting actin filament severing and a plurality of a second agent for inhibiting actin polymerization. In a storage composition, the first and second agents are present in the composition in sufficient amounts so as to prevent cold-inducediplatelet activation. As used herein, the phrase "Cold-induced platelet activation" is a term having a particular meaning to one of ordinary skill in the art. Cold-induced platelet activation is manifested by changes in platelet morphology, some of which are similar to the changes that result following platelet activation by, for example, contact with glass. The structural changes indicative of cold-induced platelet activation are most easily identified using techniques such as light or electron microscopy. On a molecular level, cold-induced platelet activation results in actin bundle formation and a subsequent increase in the concentration of intracellular calcium. Actin-bundle formation is detected using, for example, electron microscopy. An increase in intracellular calcium concentration is determined, for example, by employing fluorescent intracellular calcium chelators. Many of the above-described chelators for inhibiting actin filament severing are also useful for determining the concentration of intracellular calcium (Tsien, R., 1980, supra.). Cold-activated platelets also have a characteristically reduced hemostatic activity in comparison with platelets that have not been exposed to cold temperatures . These differences in hemostatic activity are reflected in differences in actin polymerization activity. Accordingly, various techniques are available to determine whether or not platelets have experienced cold-induced activation. such techniques can be used to select the concentrations of first and second agents that are necessary to prevent cold-induced platelet activation.

The invention further embraces pharmaceutical compositions containing cryopreserved platelets that have preserved hemos l matic activity. Hemostatic activity refers broadly to the ability of platelets to mediate bleeding cessation. Various assays are available for determining platelet hemostatic activity (Bennett, J. S. and Shattil, S. J., 1990, "Platelet function," *Hematology*, Williams, W. J., et al., Eds. McGraw Hill, pp 1233–1250). However, demonstration of "hemostasis" or "hemostatic activity" ultimately requires a demonstration that platelets infused into a thrombocytopenic or thrombopathic (i.e., non-functional platelets) animal or human circulate and stop natural or experimentally-induced bleeding.

Short of such a demonstration, laboratories use in vitro tests as surrogates for determining hemostatic activity. These tests, which include assays of aggregation, secretion, platelet morphology and metabolic changes, measure a wide variety of platelet functional responses to activation. There is, we believe, no in vitro method that can be directly translated into the in vivo setting. However, we believe that the tests disclosed herein are reasonably indicative of hemostatic function in vivo. Short of transfusion studies in animals and humans, we can definitely state only that the methods disclosed herein prevent the morphological changes associated with cold-induced platelet activation and loss of in vitro responsiveness of platelets and that presumably, this translates into improved hemostasis in vivo. (see also Slichter, S. J., 1981 *Vox Sauq* 40(Suppl 1):72–86). )

Figure 5:
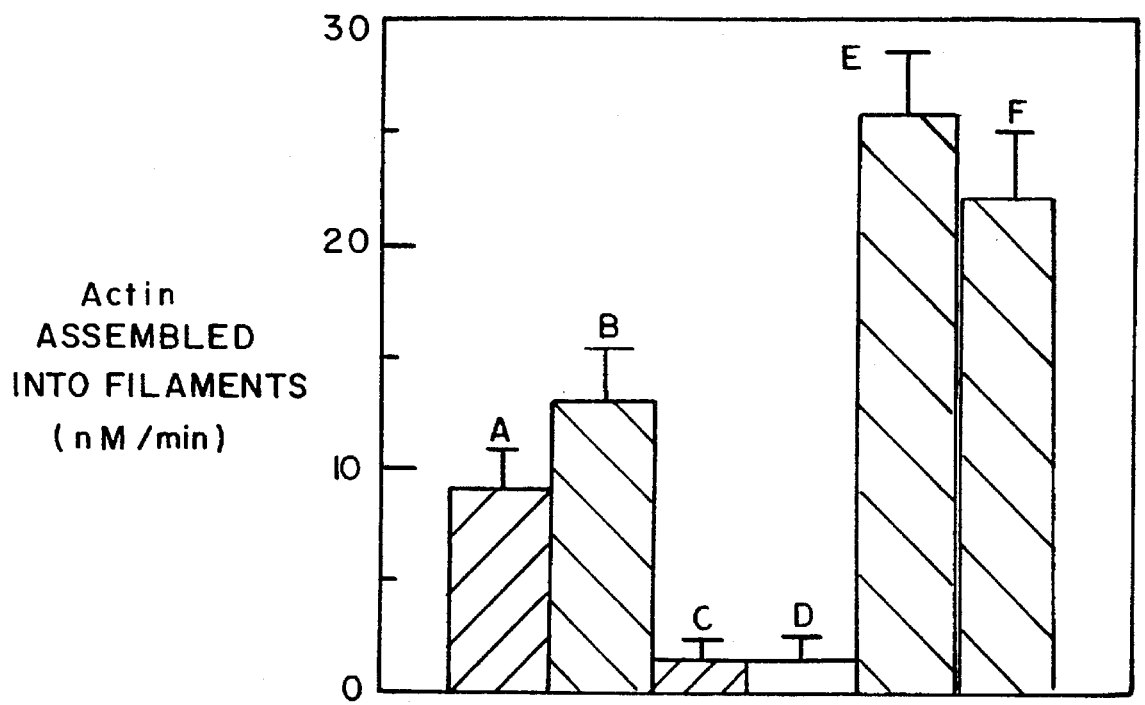
FIG. 5 graphically illustrates the prevention of cold-induced platelet activation in platelets treated with quin-2AM and cytochalasin B.

One indirect measure of hemostatic activity is the ability of platelets to assemble actin monomers onto actin filaments. Freshly obtained platelets, which have not been subjected to cold temperatures, are hemostatically afttire and have substantial amounts of actin polymerization activity. Platelets that have been subjected to cold temperatures have increased basal polymerized actin, impaired survival, are less hemostatically active (Murphy, P. H. and Gardener F. H., 1969 *N. Engl. J. Med.* 280:1094–1098; Handin, R. I. and Valeri, C. R., 1973 *N. Engl. Med.* 285:538–543) and have impaired actin polymerization activity in response to thrombin following rewarming (FIG. 5). In contrast, the cryopreserved platelets of the instant invention have an actin polymerization activity that is greater than the actin polymerization activity of the cold-treated platelets. Thus "preserved hemostatic activity" can be defined functionally (e.g., in terms of an actin polymerization activity) to refer to an amount of hemostatic activity that is greater than the hemostatic activity of a cold-treated platelet. In a preferred embodiment, the cryopreserved platelets have a hemostatic activity (and corresponding actin polymerization activity) approaching that of a platelet which has never been exposed to cold temperatures. Various assays are available for measuring actin polymerization and thereby obtaining a measure of platelet hemostatic activity (see e.g., the pyrene-labeled rabbit skeletal muscle actin polymerization rate assay, Hartwig, J. and Janmey, P., 1989 *Biochim. Biophys. Acta.* 3030:64–71).

As used herein, "actin filament severing" refers to the disruption of the non-covalent bonds between subunits comprising actin filaments. Actin filament severing in the platelet, presumably by gelsolin, requires an increasein the intracellular concentration of free calcium. Accordingly, in a preferred embodiment, the first agent for inhibiting actin filament severing is an intracellular calcium chelator. Exemplary intracellular calcium chelators include the lipophillic esters (e.g., acetoxymethyl esters) of the BAPTA family of calcium chelators, e.g., QUIN, STIL, FURA, MAPTA, INDO, and derivatives thereof. See Cobbol and Rink, 1987, supra. for a discussion of these intracellular chelators.

BAPTA is an acronym for 1,2-bis(2-aminophenoxy) ethane N,N,-N ',N '-tetraacetic acid. BAPTA and "BAPTA-like" compounds share a high selectivity for calcium over magnesium. As used herein, "BAPTA-like" refers to substituted derivatives of BAPTA and BAPTA-analogues which retain the essential calcium-chelating characteristics of the parent (BAPTA) compound (see U.S. Pat. No. 4,603,209, issued to Tsien, R., et al., the contents of which patent are incorporated herein by reference). By this definition, "BAPTA-like" compounds include compounds such as quin-1, quin-2, stil-1, stil-2, indo-1, fura-1, fura-2, fura-3, and derivatives thereof.

As used herein, quin-1 means 2-[[2-bis(carboxymethyl) amino]-5-methylphenoxy]methyl]-8-[bis(carboxymethyl) amino]-quinoline.

As used herein, quin-2 means 2-[[2-[bis(carboxymethyl)amino]-5-methylphenoxy]-6-methoxy-8-[bis(carboxymethyl)amino]quinoline.

As used herein, stil-1means 1-(2-amino-5-[2-(4-carboxyphenyl)-E-ethenyl-1]phenoxy)-2-(2'-amino-5'-methyl phenoxy)ethane-N,N,N',N'-tetraacetic acid.

As used herein, stil-2 means 1-(2(2-amino-5-[(2-(4-N,N-dimethylaminosulfonylphenyl)-E-ethenyl-1-]phenoxy)2-(2'-amino-5'methylphenoxy)ethane-N, N,N',N'-tetraacetic acid.

As used herein, indo-1 means 1-(2-amino-5-[6-carboxyindolyl-2]1-phenoxy)    -2-(2'-amino-5'-methylphenoxy) ethane-N,N,N',N'-tetraacetic acid.

As used herein, fura-1means 1-(2-(4-carboxyphenyl)-6-amino-benzofuran-5-oxy)-2-(2'-amino-5'-methylphenoxy) ethane-N,N,N',N'-tetraacetic acid.

As used herein, fura-2means 1-(2-(5'-carboxyoxazol-2'-yl)-6-aminobenzofuran-5-oxy)-2-(2'-amino-5'methylphenoxy)ethane-N,N,N',N'-tetraacetic acid.

As used herein, fura-3 means 1-(2-(4-cyanophenyl)-6-aminobenzofuran-5-oxy)-2-(2'-amino-5'-methylphenoxy) ethane-N,N,N',N'-tetraacetic acid.

The chemical structures for the above-identified calcium chelators are illustrated in U.S. Pat. No. 4,603,209, the contents of which patent have been incorporated by reference.

As used herein,ithe phrase "pharmaceutically acceptable esters" (of the intracellular chelators) refers to lipophillic, readily hydrolyzable esters which are used in the pharmaceutical industry, especially alpha-acyloxyalkyl esters. See generally, references Ferres, H., 1980 *Chem. Ind.* pp. 435–440, and Wermuth, C. G., 1980 *Chem. Ind.* pp. 433–435.

In a preferred embodiment, the intracellular chelator is the acetoxymethyl ester of quin-2(Tsien, R., et al. (1982) *J. Cell. Biol.* 94:325–334). Esterification trans forms the hydrophilic chelator into a lipophillic derivative that passively crosses the plasma membrane, and once inside the cell, is cleaved to a cell-impermeant product by intracellular esterases. Preliminary biological tests of BAPTA and its lipophillic derivatives have so far revealed little or no binding to membranes or toxic effects following intracellular microinjection (Tsien, R., supra.). Additional examples of intracellular calcium chelators are described in "Handbook of fluorescent Probes and Research Chemicals," 5th edition, distributed by Molecular Probes, Inc., Eugene, Oreg.

We believe that addition of an intracellular calcium chelator mediates severing by preventing activation of gelsolin. Accordingly, as used herein, the phrase "agents for inhibiting actin filament severing" also embraces agents which directly inhibit gelsolin severing by affecting the platelet polyphosphoinositide . Such agents include, for example, phosphotidylinositol 4-phosphate, phosphotidylinositol 4,5-bisphosphate and compounds structurally related thereto (Janmey, P. and Stossel, T., 1987 *Nature* 325:362–365; Janmey, P., et al., 1987 *J. Biol. Chem.* 262:1228–12232).

The second agent (required for preventing cold-induced platelet activation) inhibits barbed end actin polymerization. As used herein, "actin polymerization" refers to the process by which actin monomers ("G-actin") are assembled onto the fast-growing ("barbe end") of actin filaments ("F-actin"). Exemplary inhibitors of actin polymerization include the class of fungal metabolites known as the cytocha asins and derivatives thereof (see e.g., "Biochemicals and Organic Compounds for Research and Diagnostic Reagents" 1992, Sigma Chemical Company, St. Louis, Mo.).

Cytochalasin B is one of the best characterized of the cytochalasins. In addition to inhibiting actin polymerization, cytochalasin B enhances the rate at which adenine nucleotides exchange on actin molecules and the rate of ATP hydrolysis to ADP and orthophosphate. Cytochalasin B is also known to inhibit the glucose transporter of eukaryotic cell membranes. The dihydro-derivatives of cytochalasins B and D inhibit actin polymerization but do not exhibit this membrane-specific effect.

Despite the known interactions between cytochalasin B and biologically important proteins such as actin, few studies have been directed toward assessing toxicity of the cytochalasins. In vitro cell culture studies have shown cytochalasin B to be non-cytotoxic at concentrations up to 100 ug/ml (200 vM) for relatively short periods of time (about 2 hours) (Tsuyruo, et al., 1986 *Biochem. Pharmacol.* 35:1087–1090). Prolionged exposure of the cells in vitro results in reversible cytotoxicity with the cytoxic effect eliminated upon removal of cytochalasin B from ithe cellular environment (Lipski, K., et al., 1987 *Anal. Biochem.* 161:332–340).

Few studies have been conducted with the cytochalasins in vivo (see EP patent publication number 0 297 946 A2, published 04.01.89). The tissue distribution and toxicity ($LD_{50}$=50 mg/kg) of cytochalasin B following intraperitoneal administration to mice has been reported (Lipski, K., et al., supra.). Lipski et al. further report that cytochalasin B distributed rapidly into liver, renal fat, kidney, intestines mesentery, pancreas, spleen, and blood cells and was cleared from all but liver within 24 hours. However, only 35% of the injected cytochalasin B was recovered within a few minutes following injection, isuggesting that rapid oxidation of cytochalasin B toicytochalasin A, followed by sequestering of cytochalasin A in tissues, may account for the low recovery of cytochalasin B shortly after injection (Lipski, K., et al., supra.). In contrast to cytochalasin B, dihydro-cytochalasin B is not subject to oxidation to cytochalasin A. We believe that the concentration of cytochalasin remaining in cryopreserved platelets will be sufficiently low so that toxicity and/or sequestering of the cytochalasin will not be an issue. However, to avoid potential sequestering of a cytochalasin oxidation product (e.g., cytochalasin A) in tissue, the dihydro-derivatives of the cytochalasins are employed in a preferred embodiment. In a most preferred embodiment, the second agent for inhibiting actin polymerization is dihydro-cytochalasin B.

It is believed hat the cytochalasins inhibit actin polymerizatio by competing with endogenous barbed end capping agents, e.g., gelsolin, and reducing the rate of monomer addition to the barbed end of growing filaments. Based upon biochemical studies of the interactions between gelsolin and actin in vitro (Examples 1 and 2), we believe that a class of membrane lipids, the polyphosphoinositides (ppIs), mediate the dissociation of gelsolin and related molecules from the barbed ends of actin filaments. While much remains o be learned about these reactions, current information (Janmey, P. A., and Stossel, T., 1989 *J. Biol. Chem.* 264:4825–4831) suggests that eithe biosynthesis or rearrangement of ppIs in response toiplatelet activating stimuli leads to aggregates of these lipids that induce the removal of gelsolin from the barbed ends of actin filaments and the removal of ertain actin monomer binding proteins from actin subunits.

Figure 3:
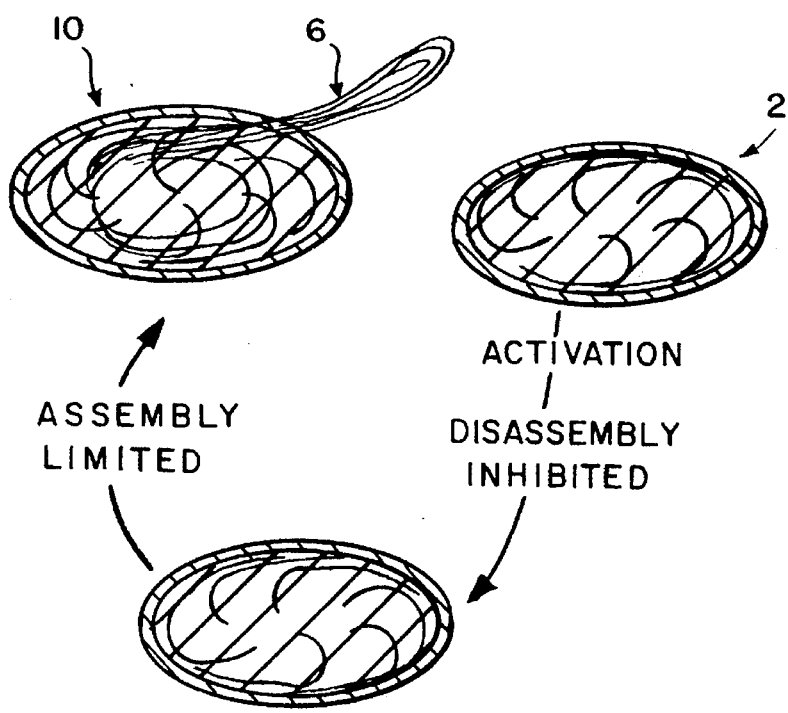
FIG. 3 schematically illustrates actin remodeling during activation of calcium chelated platelets.

That the uncapping of gelsolin molecules from the barbed ends of actin filaments (presumed to be mediated by ppIs) is separate from the calcium-dependent severing step was demonstrated by contacting platelets with quin-2AM prior to activation with thrombin (Example 2). FIG. 3 schematically illustrates the actin remodeling events that occurred during activation of the quin-2AM (calcium-chelated) platelets. Quin-2AM prevented the swelling and actin filament severing as sociated with platelet activation as well as the subse ent extension of lamellipodial networks. Instead oil collecting into filopodia, the actin bundles appearing in activated Quin-2AM-treated platelets wound repeatedly around the interior of the platelet in dense coils, distorting gross platelet morphology. Subsequent addition of calcium to the extracellular medium resulted in fragmentation of the bundles and rounding of the distorted platelets (Example 2). The letter result suggests that the addition of extracellular calcium can supplement the extracellular calcium stores to overcome intracellular calcium chelation. In view of these results, we believe that intracellular calcium chelation inhibits actin filament severing by gelsolin but does not effect the ppI-mediated uncapping of core actin filaments or the desequestration (i.e., dissociation of actin monomer binding proteins) of actin monomers and assembly of the monomers onto uncapped core filaments to generate filopodial bundles. Since we believe that cold-induced changes in ppIs leads to the uncapping of gelsolin-blocked actin filaments, agents such as peptides in the gelsolin sequence or peptides from a gelsolin-related protein (e.g., villin) that bind to ppIs and inhibit gelsolin binding to ppIs (Janmey P. A. et al., *J. Biol. Chem.* 267:11828–11838), also theoretically prevent cold-induced uncapping of filament by preventing actin filament severing. A patent application d sclosing the above-described peptides has been filed (U.S. application Ser. No. 07/898607), the contents of which patent application are incorporated herein by reference.

In a preferred embodiment, quin-2AM is the first agent for inhibiting actin filament severing and cytochalasin B or dihydro-cytochalasin B is the second agent for inhibiting actin polymerization. As used herein, the "agents for inhibiting actin polymerization" include inhibitors having a similar mode of inhibition as the cytochalasins (presumably ppI-induced actin assembly), as well as inhibitors of actin polymerization having alternative mechanisms.

Other xenobiotics having similar actions as the cytochalasins on platelet actin assembly include the Coelenterate-derived alkaloids, the latrunculins; the mushroom toxins, the virotoxins; and chaetoglobosins from different fungal species. Additional agents known to inhibit act in polymerization include actin monomer-binding proteins, profilin, thymosin, the vitamin D-binding protein (Gc globulin), DNAase I, actin-sequestering protein-56 (AsP-56), and the domain 1 fragments of gelsolin and other actin filament-binding proteins (see e.g., Kwiatkowski, O. J., et al., 1989 *J. Cell Biol.* 108:1717–1726; Way, et al. 1989 *J. Cell Biol.*

109:593–609; Hartwig, J. H. and Kwiatkowski, O. J. 1991 *Curr. Opinion Cell Biol.* 3:87–97; Vanderkerkhove, J. and Vancompernolle, K., 1992 *Curr. Opinion Cell Biol.* 4:36–42). In addition, ADP-ribosylated actin reportedly acts like a barbed end-capping protein and inhibits barbed end actin assembly (Aktories, K. and Wegner, A., 1989 *J. Cell Biol.* 109:1385. Accordingly, agents which ADP-ribosylate actin e.g., certain bacterial toxins such as *Clostridium botulinum* C2 and iota toxins, are embraced within the meaning of agents for inhibiting actin polymerization. Regardless of the mechanism of inhibition, the actin polymerization inhibitors have in common the ability to penetrate the plasma membrane.

The inhibitor of actin polymerization, may be contacted with the platelets at any time prior to subjecting the platelets to the cryopreservation temperature. Accordingly, the second agent may be contacted with the platelets at the same time as the first agent is added or before or after addition of the first agent. In a preferred embodiment, the first agent is contacted with the platelets before contacting the second agent with the platelets.

The agents are added to platelets that are kept between about room temperature and 37° C. Following treatment, the plate ets are cooled to about 4° C. In a preferred embodiment, the platelets are collected into a platelet pack or bag according to standard methods known to one of skill in the art. Typically, blood from a donor is drawn into a primary bag which may be joined to at east one satellite bag, all of which bags are connected and sterilized before use. In a preferred embodiment, the platelets are concentrated (e.g. by centrifugation) and the plasma and red blood cells are drawn off into separate satellite bags (to avoid modification of these clinically valuable fractions) prior to sequentially adding the first and second agents. Platelet concentration prior to treatment also minimizes the amounts of first and second agents required for cryopreservation, thereby minimizing the amounts of these agents that are eventually infused into the patient.

In a most preferred embodiment, the first and second agents are contacted with the platelets in a closed system, e.g. a sterile, sealed platelet pack, so as to avoid microbial contamination. Typically, a venipuncture conduit is the only opening in the pack during platelet procurement or transfusion. Accordingly, to maintain a closed system during treatment of the platelets with the first and second agents, the agents are placed in a relatively small, sterile container which is attached to the platelet pack by a sterile connection tube (see e.g., U.S. Pat. No. 4,412,835, the contents of which are incorporated herein b reference). The connection tube is reversibly sealed according to methods known to those of skill in the art. After the platelets are concentrated, e.g. by allowing the platelets to settle and squeezing the plasma out of the primary pack and into a satellite bag according to standard practice, the seal to the container(s) including the first and second agents is opened and the agents are introduced into the platelet pack. In a preferred embodiment, the first and second iagents are contained in separate containers having separate resealable connection tubes to permit the sequential addition of first and second agents to the platelet concentrate.

Following contact with the first and second agents, the treated platelets are stored at a cryopreservation temperature. As used herein, "cryopreservation temperature" refers to a temperature that is less than standard platelet storage temperatures, e.g., less than about 22° C. In a preferred embodiment the cryopreservation temperature ranges from about 0° to about 4° C. In contrast to platelets stored at, for example, 22° C., platelets stored at cryopreservation temperatures have substantially reduce metabolic activity. Thus, platelets stored at 4° C. are metabolically less active and therefore do not generate large amounts of $CO_2$ compared with platelets stored at, for example, 22° C. (Slichter, S., 1981, supra.). Dissolution of $CO_2$ in the platelet matrix results in a reduction in pH and a concommittant reduction in platelet viability (Slichter, S., 1981, supra.). Accordingly, conventional platelet packs are formed of materials that are designed an constructed of a sufficiently permeable material to maximize gas transport into and out of the pack ($O_2$ in and $CO_2$ out). The prior art limitations in patelet pack design and construction are obviated by the instant invention, which permits storage of platelets at cryopreservation temperatures, thereby substantially reducing platelet metabolism and diminishing the amount of $CO_2$ generated by the platelets during storage.

According to another aspect of the invention, a method for making a pharmaceutical preparation for administration to a mammal is provided. The method comprises preparing the above-described cryopreserved platelet preparation, warming the platelet preparation, neutralizing the first and second agents and placing the neutralized platelet preparation in a pharmaceutically acceptable carrier. In a preferred embodiment, the crycpreserved platelets are warmed to room temperature (about 22° C.) prior to neutralization. In a most preferred embodiment, the platelets are contained in a pharmaceutically acceptable carrier prior to contact with the first and second agents and it is not necessary to place the platelet preparation in a pharmaceutically acceptable carrier following neutralization.

As used herein, the terms "neutralize" or "neutralization" refer to a process by which the first and second agents ar rendered substantially incapable of further action in the preparation as agents for inhibiting actin filament severing and inhibiting actin polymerization respectively. In a preferred embodiment, the cryopreserved platelets are neutralized by dilution, e.g., with a suspension of red blood cells. Alternatively, the treated platelets can be infused into the recipient which is equivalent to dilution in millimolar calcium and into a red blood cell suspension. This method of neutralization advantageously maintains a closed system and minimizes damage to the platelets.

An alternative method to reduce toxicity is by inserting a filter in the infusion line, the filter containing, e.g. activated charcoal or an immobilized anti-cytochalasin antibody, to remove the first and second agents. Either or both of the first and second agents also may be removed or substantially diluted by washing the treated platelets. In instances in which the first agent is a intracellular calcium chelator, the first agent is preferably neutralized by the addition of unchelated calcium to the cryopreserved platelet preparation. The unchelated calcium is added to the preparation at a concentration in excess of the intracellular calcium chelator concentration.

The invention further provides a method for mediating hemostasis in a mammal. The method includes administering the above-described pharmaceutical preparation to the mammal. Administration of the cryopreserved platel ts may be in accordance with standard methods known in the art. According to one embodiment, a human patient is transfused with red blood cells before, after or during administration of the cryopreserved platelets. The red blood cell transfusion serves to dilute the administered, cryopreserved platelets, thereby neutralizing the first and second agents.

Also within the scope of the invention are storage compositions and pharmaceutical compositions for mediating hemostasis.

In one embodiment, the compositions comprise a pharmaceutically-acceptable carrier, a plurality of platelets, a plurality of a first agent for inhibiting actin filament severing and a plurality of a second agent for inhibiting actin polymerization. The first and second agents are present in the composition in sufficient amounts so as to prevent cold-induced platelet activation.

The criteria for selecting the amounts of first and second agents fo preventing cold-induced platelet activation are: (1) the first agent must be present in the composition in a amount which inhibits actin filament severing an (2) the second agent must be present in the composition in an amount that inhibits actin filament polymerization. Preferably, they are present in amounts whereby after cryopreservation and neutralization, the platelets have preserved hemostatic activity. The amounts of first and second agents which prevent cold-induced platelet activation can be selected by e posing a preparation of platelets to increasing amounts of these agents, exposing the treated platelets to a cryopreservation temperature and determining (e.g., by microscopy) whether or not cold-induced platele activation has occurred. Alternatively, the amounts of first and second agents can be determined functionally by exposing the platelets to varyin amounts of first and second agents, cooling the platelets as described herein, warming the treated (chilled) platelets, neutralizing the platelets and testing the platelets in a hemostatic activity assay to determine whether the treated platelets h ve preserved hemostatic activity.

For example, to determine the optimal concentrations and conditions for preventing cold-induced activation by a first agent that is an intracellular calcium chelator and by a second agent that is a cytochalasin, increasing amounts of these agents are contacted with the platelets prior to exposing the platelets to a cryopreservation temperature. The optimal concentrations of the first and second agents are the minimal effective concentrations that preserve intact platelet function as determined by in vitro tests (e.g., observing morphological change in response, to glass, thrombin, cryopreservation temperatures; ADP-induced aggregation; actin p lymerization) followed by in vivo tests indicative of hemostatic function (e.g., recovery, survival and shortening of bleeding time in a thrombocytopenic ahimal or recovery and survival of $^{51}$Cr-labeled platelets in human subjects).

New compounds also can be screened for their ability to act as first and second agents in preventing cold-induced platelet activation. The amounts of previously untested first and second agents necessary to prevent cold-induced platelet activation can be determined by selecting an amount of first agent which inhibits actin filament severing and by selecting an amount of second agent which inhibits actin polymerization. As previously noted, the severing of actin filaments is detectable by electron microscopy or other published procedures (see e.g. Janmey, P. A. and Stolssel, T. P., 1987 *Nature* 325:362–365). One method for selecting an amount of an untested first agent for inhibiting actin severing is by treating intact platelet preparations (containing increasing amounts of the first agent) with cytochalasin B (to inhibit barbed end polymerization activity), activating the polymerization-inhibited platelets (e.g., by exposure to a cryogenic temperature) and observing (by microscopy) structural changes in the polymerization-inhibited, activated platelets. The polymerization-inhibited, activated control platelets (i.e., platelets that were not exposed to first agent) exhibit actin filament severing (as observed by electron microscopy) but do not extend the lamellipodia or filopodia characteristic of actin polymerization because actin polymerization is inhibited. The polymerization-inhibited, activated platelets (exposed to increasing amounts of the first agent) exhibit decreasing amounts of actin severing (as observed by electron microscopy). According to this method, the amount of first agent which is necessary to preven cold-induced platelet activation is that amount whic empirically inhibits actin severing. For first agents that are intracellular calcium chelators, the amount of the first agent that inhibits actin severing is, in part, dependent upon the affinity and specificity of the intracellular chelator for calcium. In a preferred embodiment, the first agent is Quin-2AM which is present in the composition at a concentration of about $10^{-16}$ mole/platelet.

Similarly, various assays are available for selecting an amount f second agent that inhibits actin monomer assembly onto actin filaments (actin polymerization). For example, a pyrene-labeled actin polymerization assayihas previously been described (Hartwig, J. and Janmey, P. 1989 *Biochim. Biophys. Acta* 1010:64–71). Pyrene actin assembly onto actin filaments is completely inhibited at the barbed end by 2 uM cytochalasin B (Examples 1 and 2). Thus, cytochalasin B inhibitable activity in the pyrene-labeled polymerization assay is defined as "barbed end" actin assembly (polymerization). Accordingly, the amount of an untested second agent for inhibiting actin polymerization is determined, for example, by substituting the untested second agent for cytochalasin B in the pyrene labeled polymerization assay (using increasing amounts of the untested second agent) and selecting the concentration of second agent that inhibits actin assembly onto the barbed end of actin filaments. In a preferred embodiment, the second agent is cytochalasin B which is present in the composition at a concentration of about $10^{-}$mole/platelet. In a most preferred embodiment, the second agent is dihydro-cytochalasin B which is present in the compoisition at a concentration of about $10^{-18}$ to about $10^{-17}$ mole/platelet.

In yet another embodiment, the pharmaceutical composition comprises a plurality of platelets, a plurality of a non-naturally occurring intracellular calcium chelator, a plurality of a non-naturally occurring second agent for inhibiting actin polymerization and a pharmaceutically acceptable carrier. As used herein, the term "non-naturally occurring" refers to a molecule which is not present in platelets as they exist in circulating blood. Exemplary non-naturally occurring intracellular calcium chelators are the above-described lipophilic derivatives of the BAPTA family of calcium chelators. Exemplary non-naturally occurring second agents for inhibiting actin polymerization include the above-described cytochalasins and derivatives thereof, as well as fragments of larger molecules which are present in platelets as they exist in circulating blood.

According to yet another aspect of the invention, a composition for addition to platelets to prevent cold-induced platelet activation is provided. The composition includes a plurality of a first agent for inhibiting actin filament severing and a plurality of a second agent for inhibiting actin polymerization. The first and second agents are present in the composition in amounts that prevent cold-induced platelet activation. In a preferred embodiment, the first agent is the acetoxymethyl ester of quin-2 (quin-2AM) and the second agent is cytochalasin B.

EXAMPLES

The instant invention provides methods and pharmaceutical compositions for the cryopreservation of platelets with preserved hemostatic activity. The following examples illustrate representative utilities of the instant invention.

MATERIALS AND METHODS

A. Preparation of Resting Platelets

Human blood from healthy volunteers, drawn into 0.1 vol of Aster-Jandl anticoagulant, was centrifuged at 110 g for 10 min. The platelet-rich plasma was gel-filtered throughia Sepharose 2B column eguilibrated and eluted with a solution containing 145 mM NaCl, 10 mM Hepes, 10 mM glucose, 0.5 mM $Na_2HPO_4$, 5 mM KCl, 2 mM $MgCl_2$, and 0.3% BSA, pH 7.4 (platelet buffer). 2 U/ml apyrase was added to the platelet suspension and the cells were left standing for 60 min. at 37° C. as previously reported (Hartwig, J., and M. DeSisto, 1991 *J. Cell Biol.*112:407–425; Hartwig, J., et al. 1989 *J. Cell Biol.*109:1571–1579). To maintain cytosolic calcium at or below its resting level during cell activation, cells were loaded with 30 uM Quin-2AM during minutes 30–60 of the rest period. The effect of Quin-2was reversed by the addition of 1 mM $CaCl_2$ to the bathing media before centrifugation of the Quin 2-loaded cells onto the coverslips or after the cells had been attached and formed filopodia on the coverslip.

Glass-adherent, Quin-2 loaded cells were also treated with 1 mM $CaCL_2$ and 20 nM of the ionophore A23187 for 15 seconds (s) and then detergent permeabilized. In some cases, platelets were used directly from platelet-rich plasma by diluting it 1:20 with platelet buffer containing, in addition, 0.1 mM EGTA and 2 U/ml apyrase. The diluted cells were incubated for 30 min. at 37 ° C. to insure a resting state.

B. Activation of Platelets

Platelet suspensions were activated by the addition of 1 U/ml of thrombin (hereafter called thrombin-activated) for 15–30 seconds in studies of nucleation activity. Activation was terminated by permeabilizing the cells as detailed below. Glass activation was used for the morphological studies. Cells were glass-activated by centrifugation onto polylysine-coated glass coverslips at 250 g for 5 min. Coverslips were placed in the bottom of multiwell plates (24 or 96 wells), covered with 0.25 ml of platelet suspension, and centrifuged at 37° C. in a Sorvall HB-6000 centrifuge using multiwell carriers.

C. Fluorescence Measurement of Actin Assembly in Lysates from Resting and Activated Cells The effect of cell lysates on the rate and extent of pyrene-labeled rabbit skeletal muscle actin was determined as described previously (Hartwig, J., and P. Janmey, 1989 *Biochim. Biophys. Acta.* 1010:64–71). suspensions of resting or thrombin-activated cells at concentrations of $1.4 \times 10^8$/ml were permeabilized by the addition of 0.1 volume of 60 mM Pipes, 25 mM Hepes, 10 mM EGTA, 2 mM $MgCl_2$, 0.75% Triton and 42 nM leupeptin, 10 mM benzamidine, and 0.123 mM aprotinin to inhibit proteases (Schliwa, J., et al., 1981 *Proc. Natl. Acad. Sci. USA* 80:5417–5420). 100 ul of detergent lysate was added to 190 ul of 100 mM KCl, 2 mM $MgCl_2$, 0.5 mM ATP, 0.1 mM EGTA, 0.5 mM dithiothreitol, and 10 mM Tris, pH 7.0 and the polymerization rate ssay was started by the addition of monomeric pyrene-labeled rabbit skeletal muscle actin to a final con pentration of 2 uM. The relative contribution of nuclei with barbed or pointed ends in the cell lysates was determined by adding 2 uM cytochalasin B to the pyrene nucleation assay system. Pyrene actin assembly onto actin filament nuclei has been shown to be completely inhibited at the barbed end by 2 uM cytochalasin B. Cytochalasin B inhibitable activityin the nucleation assay is, therefore, defined as "barbed" end assembly. Activity not inhibited by cytochalasin B is considered pointed end assembly. The stability of nucleation activity in cell lysates was tested by comparing the stimulatory effect of fresh lysate on actin assembly with lysates allowed to stand for 30 s to 30 min at 37° C. before addition to the assembly assay. To determine if the measured stimulation of actin assembly and its decay with time was due to the growth of pyrene-actin addition onto cellular filaments subject to depolymerization in the diluted lysate, 0.1 uM phalloidin or phallacidin was added to the cell lysates during thei preparation to stabilize the filaments. As shown in the results, all nucleation activity present in resting and activated cells was associated with the detergent-insoluble cytoskeleton. However, we also determined that the soluble phase from cells permeabilized with detergent in the presence of EGTA contained calcium dependent nucleation activity. Detergent lysates from resting and thrombin-activated cells (30 s, 1 U/ml) were centrifuged at 10,00 g for 2 min at room temperature in a microcentrifuge,. The supernatant was removed and added to the pyrene-based nucleation assay in the presence of 1 mM EGTA or $CaCl_2$. The amount of pointed end activity in these soluble extracts was determined by adding a final concentration of 2 uM cytochalasin B to th pyrene-actin assembly assay.

The effect of inhibiting barbed end actin assembly in thrombin activated cells before detergent lysis on the amount Df nucleation activity was determined by preinc bating resting platelet suspensions with 2 uM cytochalasin B for 5 min. Because it was necessary to wash out the cytochalasin B from some of the cytoskeletons before addition of the cell lysates to the pyrene assembly assay, the cells were first attached to glass coverslips while still in the presence of cytochalasin B. This was accomplished by sedimenting 0.3 ml of cell suspension onto a 12 mm round glass coverslip for 5 min at 250 g. Individual coverslips were removed, treated with thrombin for 15 s in the presence of cytochalasin B, permeabilized with 1× PHEM-Triton buffer containing 2 uM cytochalasin s for 15 s and then washed in PHEM buffer in the presence or absence of cytochalasin B. Coverslips were then immediately assayed for their ability to promote actin filament assembly as previously described by us using glass adherent macro phage cytoskeletons (Hartwig, J., and P. Janmey, 1989 *Biochim. Biophys. Acta.*1010:64–71).

D. Morphological Studies

Light microscopy and electron microscopy of platelets and cytoskeletons were performed according to standard methods, see e.g., Hartwig, J., 1992, *J. Cell Biol.* 118(6):1421–1442. The localization of gelsolin in platelets was performed by gold labeling of cytoskeletons from resting and activated cells with antibodies to gelsolin. The affinity-purified goat anti-rabbit macrophage gelsolin IgG was described earlier (Hartwig, J. and M. DeSisto, 1991 *J. Cell Biol.* 112:407–425; Hartwig, J., and P. Shevlin, 1986 *J. Cell Biol.* 103:1007–1020).

EXAMPLE 1

Actin Nucleation Activity in Resting and Activated Cells

To understand how new filament assembly (polymerization) is initiated during cell activation, the nature and amount of nucleation activity in detergent lysates from resting and thrombin-activated cells was characterized using a pyrene-actin assembly system in vitro. As shown in Table 1, lysates of resting cells permeabilized with Triton X-100 had only a small stimulatory effect on the rate at which pyrene-actin assembled in solutions containing 0.1M KCl and 2 mM MgCl$_2$. This small increase in the rate of actin assembly by resting lysates was probably due primarily to the addition of pyrene monomers onto the slow-exchanging filament ends (pointed end of S1-labeled fibers) because addition of 2 uM cytochalasin B to lysates from resting cells, which blocks exchange at the high affinity ("barbed") ends, had only a small effect on the amount of nucleation activity measured in fthe pyrene assay. From the kinetics and extent of pyrene assembly and rates of addition of monomers to the filament ends, 2,000 pointed filament ends are present in a resting cell. Lysates from cells activated with 1 U/ml of thrombin for 15–30 s before permeabilization, however, increased the pyrene actin assembly rate three- to four-fold relative to resting lysates (Table 1). In contrast to the resting lysates, the stimulatory effect in these lysates was abolished by the addition of 2 uM cytochalasin B to the actin assembly assay (Table 1). Since cytochalasin B blocks new actin assembly in both intact, thrombin-activated platelets (Casella, J., et al., 1981 *Nature (Lond.)* 293:302–305; Fox, J. and D. Phillips, 1981 *Nature (Lond.)* 292:650–652) and in lysates from thrombin-activated cells, filament assembly in platelets must occur predominantly on the fast growing (barbed) end of filaments. Depending on the experiment, 410–570 barbed ends would have been required on average in each platelet to increase the rate of actin assembly by the determined extents (Table 1).

Before centrifugation, lysates increased the actin assembly rate by 1.528±0.11 nM s$^{-1}$ (mean±SD) relative to actin alone. Centrifugation of lysates at 10,000 g for 2 min, which sediments aggregates of cellular actin fibers but not individual actin filaments, removed 99% of the nucleation activity induced by thrombin. This result indicates that all barbed end nucleation activity measured in EGTA-containing buffer was associated with the low-speed sedimentable platelet cytoskeleton.

In all of the nucleation experiments described above, the calcium ion concentration was low because all solutions contained EGTA to chelate calcium. Although raising the calcium concentration of assay solutions into the micromolar range by addition of sufficient CaCl$_2$ had no effect on the barbed end nucleation activity hat was sedimentable in lysates of thrombin-activate platelets, the soluble fraction remaining after removal of cytoskeletons also contained a large amount of calcium-dependent actin nucleation activity (Table II). This activity was, however, in contrast to the calcium-insensitive sedimentable activity, completely unaffected by 2 uM cytochalasin B, demonstrating that it promotes actin assembly only in the pointed (non-barbed end) direction. No calcium-activated soluble nucleation activity was detectable in lysates from resting cells.

TABLE I

| | Calcium-insensitive Cytoskeletal Nucleation Activity | | | | | |
|---|---|---|---|---|---|---|
| Treatment | Assembly rate (Pointed end) | Assembly rate (barbed end*) | Subunits added to pointed ends** | Subunits added to barbed ends*** | Pointed nuclei/platelet | Barbed nuclei/platelet |
| | nM s$^{-1}$ | nM s$^{-1}$ | ×10$^{10}$s$^{-1}$ | ×10$^{10}$s$^{-1}$ | | |
| Resting | 0.21 ± 0.04 | 0.04 ± 0.02 | 3.7 ± 0.70 | 0.7 | 2,000 ± 380 | 50 ± 25 |
| Activated | 0.24 ± 0.02 | 0.58 ± 0.03 | 4.3 ± 0.35 | 10.4 | 2,500 ± 200 | 410 ± 15 |

*The barbed end assembly rate is calculated by subtracting the assembly rate in the presence of 2 μM cytochalasin B from the assembly rate in the absence of cytochalasin B.
**Initial pointed end addition rate in 2 μM actin solution was 1.2 subunits s$^{-1}$.
***Initial barbed end addition rate in 2 μM actin solution was 18 subunits s$^{-1}$.

In reference to Table I, gel-filtered platelets were suspended to a concentration of 1.4×10$^8$/ml in platelet buffer, rested for 30 minutes at 37° C., and then treated with or without 1 U/ml of thrombin for 15 s. The cells were permeabilized by the addition of 0.1 vol of 10× PHEM buffer (Schliwa, M., et al., 1981 *Proc. Natl. Acad. Sci. USA* 80:5417–5420) containing 0.75% Triton X-100 and protease inhibitors. 110 μl of platelet lysate wes added to 180 μl of 0.1M KCl, 0.5 mM ATP, 2 mM MgCl$_2$, 0.3 mM beta-mercaptoethanol, and 2 mM Tris, pH 7.0. The rate assay was started by the addition of pyrene-labeled actin monomers to a final concentration of 2 μM. The final volume was 0.3 ml. 2 μM cytochalasin B was added to determine the amount of total activity related to the barbed filament end. There were 1.4×10$^7$ platelets per assay. Data are expressed as mean ± SD, n=4.

TABLE II

| | Calcium-sensitive Soluble Nucleation Activity | | | |
|---|---|---|---|---|
| Treatment | 2 μM CB | Assembly Rate* | Subunits added to pointed ends** | Pointed nuclei/platelet |
| | | nM s$^{-1}$ | ×10$^{10}$s$^{-1}$ | |
| Resting | + | ND | — | — |
| Resting | | ND | — | — |
| Activated | + | 0.55 ± 0.02 | 1.0 ± 0.05 | 5,000 ± 250 |
| Activated | | 0.54 ± 0.03 | 0.97 ± 0.05 | 4,850 ± 243 |

In reference to Table II, lysates were prepared from resting thrombin-treated cells with detergent and centrifuged in a Sorvall Microspin 12S at 13,000 rpm for 1 min. Nucleation activity remaining in the supernatant after removal of the cytoskeletal fraction was determined. Centrifugation of lysates removed all cytoskeletal-associated nucleation activity from the resultant supernatants. There were 2.0×10 platelets per assay. The data are expressed as mean ± SD, n=4. NC=not detectable. The barbed end assembly rate, initial pointe d end addition rate and initial barbed end addition rate are as described for Table I.

EXAMPLE 2

Evidence for the Role of Calcium in Cytoskeletal Rearrangements Occurring with Platelet Activation A. Quin-2-loaded Platelets Attach to Glass Extend Filopodia, but Do Not Spread.

Loading platelets with 30 uM Quin-2AM had no effect on the structure of the resting cells observed in the light microscope or cytoskeletons prepared from these resting cells (data not shown). However, the morphologies of glass-activated cells differed from untreated cells spreading on coverslips. As illustrated schematically in FIG. 3, platelets loaded with Quin-2and then glass activated extend filopodia but not lamellipodia. Filopodia were 2–5 um in length, thicker in diameter relative to those from control cells, and ad bulbous endings (FIG. 3). Although filopodia extended from these cells, the cell shape remained discoid with dimensions near those of the resting cell. In the electron microscope, the surface of intact cells retained the pits of the open canalicular system (OCS). While most of the cells had filopodia, some other morphologies were also apparent. Most glass-activated Quin-2-loaded platelets extended ane prominent filopod, but a few simply elongated or made spherical protrusions at their margins. As detailed below, these different morphologies resulte from related cytoskeletal actin rearrangements. If Quin-2-loaded cells were bathed in medium containing millimolar calcium, normal spreading of cells resulted oni the glass surfaces (i.e., cells spread both lamellipodia and filopodia.

When observed in the electron microscope, cytoskeletons prepared from Quin-2-loaded and glass-activated cells lack lamellipodial networks at their margins. Instead, these cytoskeletons are composed exclusively of long filaments running parallel to the cell margin. These filaments appear to derive from filaments originating in the cell center which turn an run along the cytoskeletal edges. Filopodia in cytoskeletons from Quin-2-loaded cells are filled with actin filaments originating near the middle of the cytoskeleton, but these filaments do not end near the tip B of the filopodia as in control cells. Instead, these filaments make U-turns and run back into the body of the cytoskeleton. These filament loops, therefore, appear to produce the bulbous enlargements at the ends of filopodia in these cells. Not all actin fibers entering filopods make U-turns. A few of the filaments within filopodia end near their tips. Examination of cytoskeletons from cells displaying simply an elongated shape without a filopod reveals them to have internal bundles of filaments. Fibers coming off the ends of these bundles turn and run in parallel with filaments in the cytoskeletal margins or turn and run back toward the middle of the cytoskeletons instead of exiting to form filopodia. Cytoskeletons of bleb forms also share these features. Blebs at the cytoskeletal edges are composed of loops of actin filaments with some underlying straight filaments.

B. Quin-2Loading Diminishes Thrombin-stimulated Nucleation Activity.

Nucleation activity in lysates from Quin-2-loaded and control cells was compared after thrombin activation. Lysates from activated cells loaded with Quin-2had only 28% of the nucleation activity of lysates from untreated and activated cells when assayed immediately. When directly compared, the total number of nuclei was equivalent to that remaining in control lysates incubated for 2 min. before addition to the assembly assay. Although the total nucleation activity was reduced, its stability was increased in lysates of Quin-2-chelated, thrombin-activated cells. Nucleation activity in the detergent lysates from Quin-2-loaded cells was more stable, and no loss in its activity occurred in lysates incubated for as long as 10 min. before addition to the assembly assay. In contrast to lysates from unchelated cells, phalloidin had no effect on the nucleation activity in lysates from Quin-2-loaded cells. The stability of actin filament nuclei in the Quin-2-loaded cells could result either from their being considerably longer in length compared with control cells or from their being coated with proteins that retard depolymerization. The former alternative finds support in the electron microscope where the periphery of Quin-2-loaded and activated cells were replete with long fibers. Filaments of lengths greater than or equal to 1.5 um would have survived to, nucleate in the assay.

The above experiments have shown that long actin filaments preexisting in resting platelets shorted in a calcium-dependent fashion during cell activation with thrombin or glass stimuli and that these short filaments then become templates for the assembly of lamellipodial networks . Two possibilities exist for the formation of this short filament population during cell activation. Filaments forming the resting cytoskeleton could be fragmented into smaller pieces or the resting actin cytoskeleton could disassemble to monomers and be replaced by a new population of short filaments. The following experiments address the mechanism of this short filament formation.

C. Readdition of Calcium to Quin-2-loaded Cells Rapidly Dissolved the Actin Filament Bundles in These Cells.

Filopodial forms enerated by Quin-2-loading and glass activation of platelets were rapidly converted to forms resembling activated, unchelated platelets when the buffer bathin the cells was replaced with one containing millimolar calcium. Bundles were rapidly reorganized into lamellipodial networks. The effect of added external calcium in the presence of the ionophore A23187 was more dramatic. Within seconds, the cytoskeletons of previously chelated cells that contained large actin filament bundles were completely disrupted, leaving a fibrous residue lacking actin filament. This disruption occurred too rapidly to be explaine, by filaments depolymerizing from their ends. Many actin filaments were also scattered over the surface of the coverslip.

D. Cytochalasin B Does Not Affect the Amount of Nucleation Activity in Lysates of Activated Cells.

In the experiment described above, cytochalasin B added to lysates served as a test for the direction (barbed versus pointed) of actin assembly off of nuclei present. In the following experiments, cytochalasin B incubated with intact platelets and later diluted to concentrations in lysates below which it blocks actin assembly permitted the assessment of morphological changes nd determination of whether actin nucleation activity appears after platelet activation under a condition in which the bulk of cytoplasmic actin cannot assemble.

The generation of nucleation activity after thrombin treatment in the presence of cytochalasin B was demonstrated using the pyrene-labeled actin assembly assay. As shown in Table III, cytoskeletons from thrombin-activate and cytochalasin B-treated cells stimulate the rate of pyrene-actin assembly in vitro four-fold compared with resting cells incubated with cytochalasin B in parallel (to levels comparable to lysates from thromb n-activated cells) when cytochalasin was present while the cells were undergoing activation ut washed away before determining nucleation activity. Cytochalasin B treatment of resting cells did not by itself result in nucleation activity. In addition, the rate of actin assembly from the barbed filament ends was near that in cells not exposed to cytochalasin B (compared with Table I). Therefore, these experiments demonstrate that the short filaments found in cytoskeletons from activated cells do not derive from the de novo assembly of actin monomers onto some unspecified barbed end nucleating gent, because cytochalasin B did not inhibit their formation.

To demonstrate that the short actin filaments formed in cells activated in the presence of cytochalasin were calcium dependent, the normal rise in cytosolic calcium was inhibited by loading these cells with Quin-2 and then attaching them to glass by centrifugation in the presence of cytochalasin B. The morphology of these cells was unchanged from that of resting cells and a cytoskeleton prepared from these cells resembles the structure of the resting platelet cytoskeleton. The cytoeskeleton of such cells was discoid and covered with its dense membrane skeleton.

TABLE III

Effect of Cytochalasin B on the Nucleation Activity in Activated Cytoskeletons

| Treatment | Assembly rate (pointed end) | Assembly rate (barbed end*) | Subunits added to pointed ends** | Subunits added to barbed ends*** | Pointed nuclei/ platelet | Barbed nuclei/ platelet |
|---|---|---|---|---|---|---|
| | $nM\ s^{-1}$ | $nM\ s^{-1}$ | $\times 10^{10} s^{-1}$ | $\times 10^{10} s^{-1}$ | | |
| Resting | 0.55 ± 0.15 | 0.18 ± 0.23 | 9.95 ± 3.30 | 2.0 | 1,980 ± 660 | 50 + 20 |
| Activated | 0.55 ± 0.18 | 1.59 ± 0.30 | 9.95 ± 3.30 | 39.0 | 1,980 ± 660 | 380 + 50 |

In reference to Table III, resting platelets were incubated with 2 μM cytochalasin B for 5 min, then adhered by centrifugation to 12-mm round glass coverslips coated with polylysine. Cells on the coverslips were exposed to 1 U/ml of thrombin for 30 s in the presence of cytochalasin B and then permeabilized with PHEM-Triton buffer. Some coverslips were washed rapidly (1–2×) through PHEM that did not contain cytochalasin to remove this agent and added to the pyrene-labeled actin assembly system. Cytoskeletons from thrombin-treated cells markedly stimulated the rate of actin assembly nucleation activity upon the removal of the cytochalasin B. Cytochalasin B treatment of resting cells did not increase the amount of nucleation activity in resting cytoskeletons. There were $4.2 \times 10^7$ platelets per assay. The data are expressed as mean ± SD, n=4. The barbed end assembly rate, initial pointed end addition rate and initial barbed end addition rate were as described in Table I.

E. Location of Gelsolin in Resting and Activated Cytoskeletons.

The results of the experiments described above implicate calcium-activated actin filament severing as an important step in the remodeling of the resting cytoskeleton into the activated form. Gelsolin accounts for 0.5% of platelet total protein, yielding a molar ratio of gelsolin to actin of about 1:80, and is an excellent candidate to cause the actin severing observed during platelet activation. Gelsolin was localized in resting and activated cytoskeletons by immunoelectron microscopy. The cytoskeletal gelsolin identified with anti-gelsolin IgG and colloidal-gold particles were found in clusters bound near the membrane skeleton-actin filament interface in thin sections. To determine whether this gelsolin was associated with the ends of actin filaments at this interface or linked to the membrane skeleton, it was localized in mechanically opened cytoskeletons (Hartwig, J. and DeSisto, M., 1991 *J. Cell Biol.* 112:407–425) from resting cells. Micrographs of these preparations demonstrated that: (a) gelsolin does not associate with the membrane skeleton per se;(b) gelsolin does associate with the actin filament core lining its surface; (c) gold particles are clustered in the core; and (d) is on the ends of at least some of the 10-nm filamentsiknocked out of the cytoskeletons by the mechanical treatment and is associated with filaments within the filamentous core to the membrane skeleton. Since the bulk of gelsolin released by detergent reatment of resting cells is gelsolin free (>95%), the large number of gold particles not bound to actin filament ends in these specimens is expected.

As the cytoskeleton changes during spreading, gelsolin also changes in its distribution from the resting condition. Gelsolin-reactive gold particles located in the lamellipodial zone of the cytoskeleton. Labelin occurred preferentially on one filament end, and less often along filaments. The filament ends decorate with gelsolin-gold were free, were attached to the substratum or pointing upward from it, or intersected the side of another filament to form T-shaped intersections. In marked contrast to resting cells, gold particles in the activated cytoskeleton were not found as large clusters. Filament ends were generally decorated with one to three gold particles. Since only one gelsolin molecule is required to cap the filament end, particle groups of one to three would therefore appear to reflect individual gelsolin molecules. The larger clusters in the restin cytoskeletons would therefore appear to reflect gelsolin clusters.

Such rearrangements of gelsolin did not occur in the Quin-2-loaded and activated cells. Gelsolin-reactive gold in these cytoskeletons was more clustered than in the resting cell cytoskeleton. Clusters lay on the sides of actin filaments instead of at their ends.

EXAMPLE 3

Cold-induced platelet Activation

Figure 4:
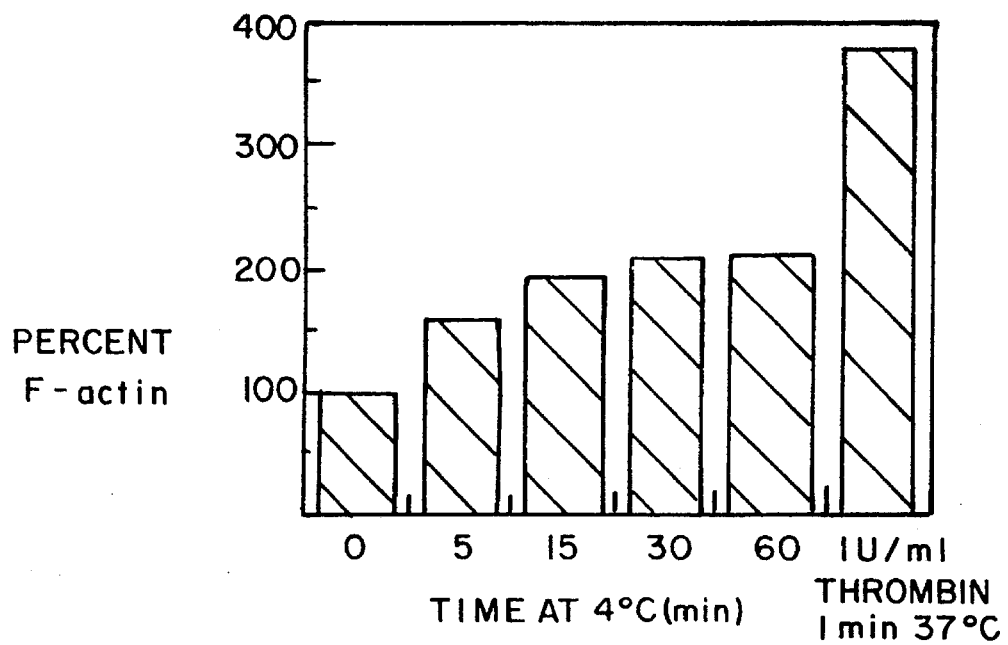
FIG. 4 graphically illustrates the time course of actin assembly in cold-exposed or thrombin-treated platelets.

Following exposure to 4° C., actin assembly over a fifteen minute period is about double the level of actin assembly in resting platelets and about one third the level of actin assembly in thrombin-activated platelets (FIG. 4). Actin polymerization was determined by measuring phallacidin binding (Havard, T. H. and Oresajo, J., 1987 *Cell Motility and the Cytoskeleton* 5:545–557).

Figure 2:
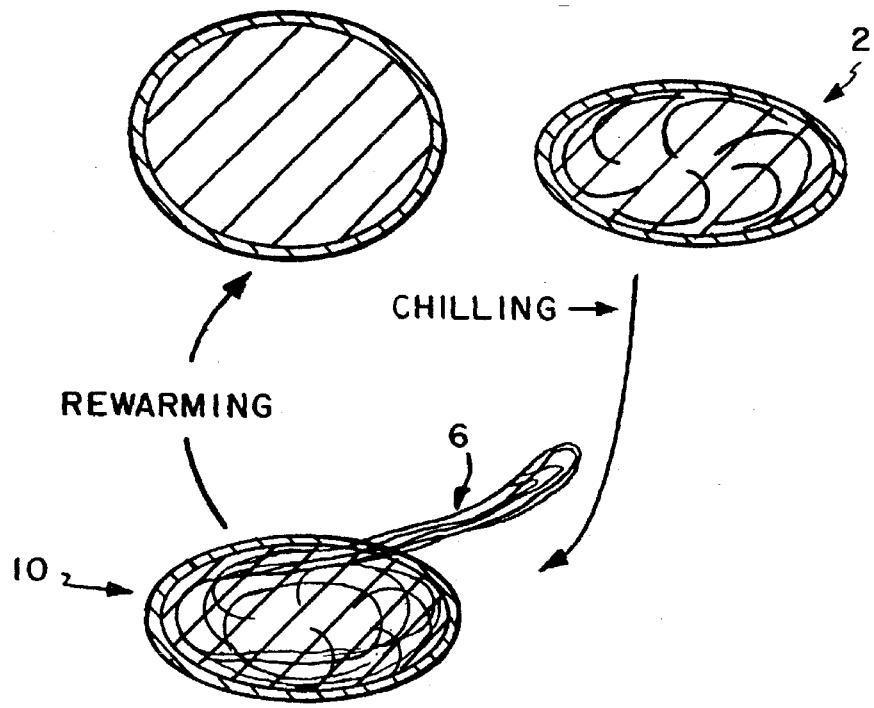
FIG. 2 schematically illustrates actin remodeling during cold-induced activation of platelets.

FIG. 2 schematically illustrates the cold-induced platelet shape distortion caused by actin filament coils. The distorted shape resembles that of Quin-2AM-treated platelets at room temperature (FIG. 3) and is consistent with the hypothesis that chilling results in th uncapping, presumably ppI-mediated, of gelsolin-capped actin filament barbed end in resting platelets and desequestration of monomers. In the absence of severing (inhibited by the Quin-2AM treatment), filament growth results in actin filament coils which distort the platelet shape.

Following rewarming, the chilled platelets regain a spherical shape, a change interpreted as "recovery" many years ago by Zucker et al. (Zucker, M. B. and Borrelli, J., 1954 *Blood* 9:602). However, the rewarmed platelets exhtbit impaired hemostatic activity (Handin, R. I. et al., 1970

*Transfusion* 10:305; Handin, R. I. and Valeri, C. R., 1972 *N. Engl. J. Med.* 285:538). Electron microscopic examination of the platelets revealed that they resemble Quin-2AM-treated plate lets to which calcium was added rather than discoid (resting platelets). These results suggest that chilling and rewarming results in a rise in platelet int acellular calcium which activates gelsolin to sever the bundles formed during chilling. However, the architecture of the resting platelet is destroyed by these events, so that subsequent activation cannot result in the normal shape changes requiredi for optimal hemostatic activity.

EXAMPLE 4

Inhibition of Cold-induced Platelet activation

The addition of an intracellular calcium chelator (Quin-2AM) and an actin assembly inhibitor (cytochalasin B) to a platelet preparation prevented cold-induced actin bundle formation and a subsequent increase in intracellular calcium concentration.

Figure 6:
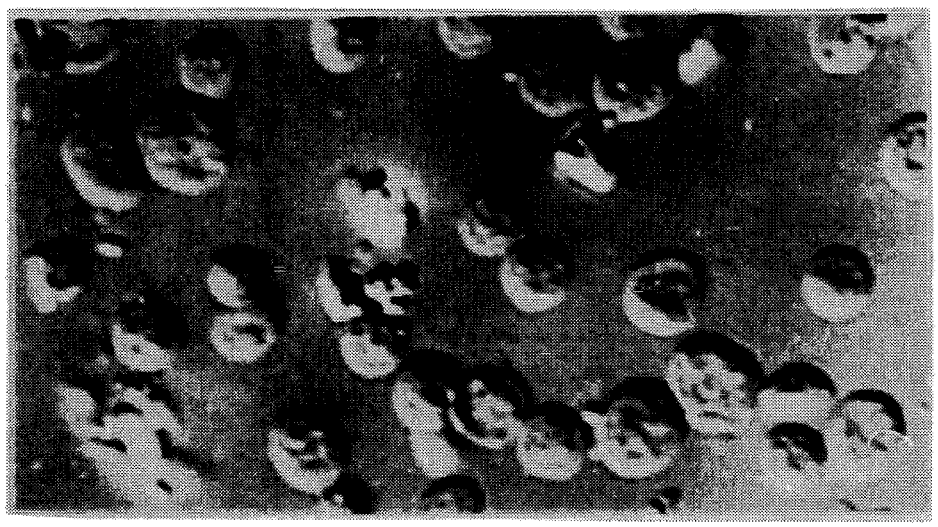
FIG. 6 illustrates the morphology of resting human platelets at 37° C.
Figure 7:
FIG. 7 illustrates the morphology of human platelets exposed to 4° C. for 90 minutes.
Figure 8:
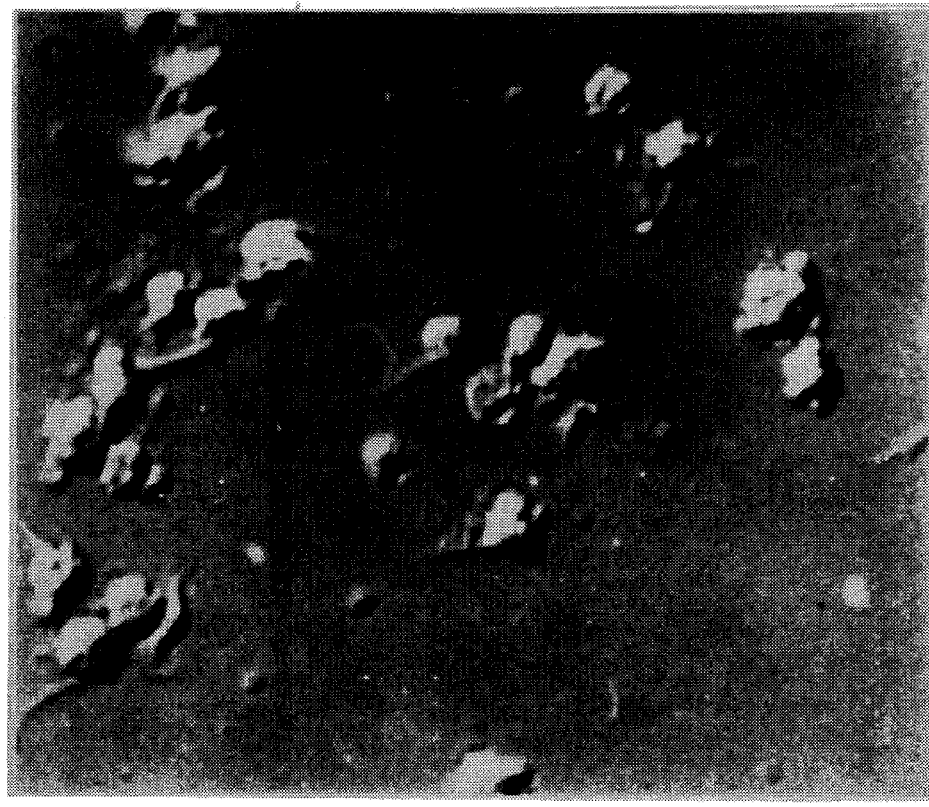
FIG. 8 illustrates the morphology of human platelets treated with 40 µM quin-2AM and exposed to 4° C. for 90 minutes.
Figure 9:
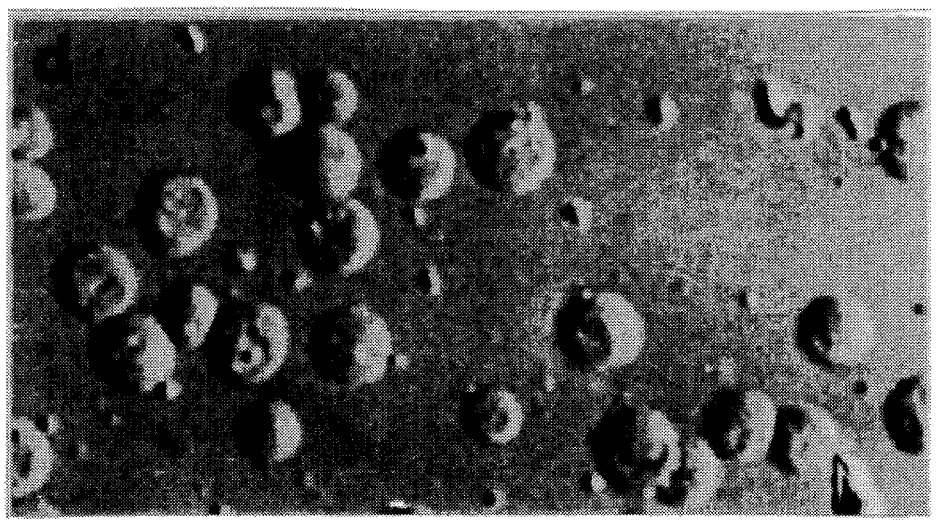
FIG. 9 illustrates the morphology of human platelets treated with 40 µM quin-2AM and cytochalasin B and exposed to 4° C. for 90 minutes.

FIGS. 6–9 illustrate the morphology of treated and/or untreated human platelets at 4° C. The morphologies of resting human platelets at 37° C. and cold-induced activated human platelets are shown in FIGS. 6 and 8, respectively. FIG. 7 illustrates the morphology of platelets treated with quin-2AM alone. FIG. 9 shows that platelets stored at 4° C. for 90 minutes remain discoid only when pre-treated with both quin-2AM and cytochalasin B. These cells were identical in shape to those maintained at 37° C. (FIG. 6).

Figure 10:
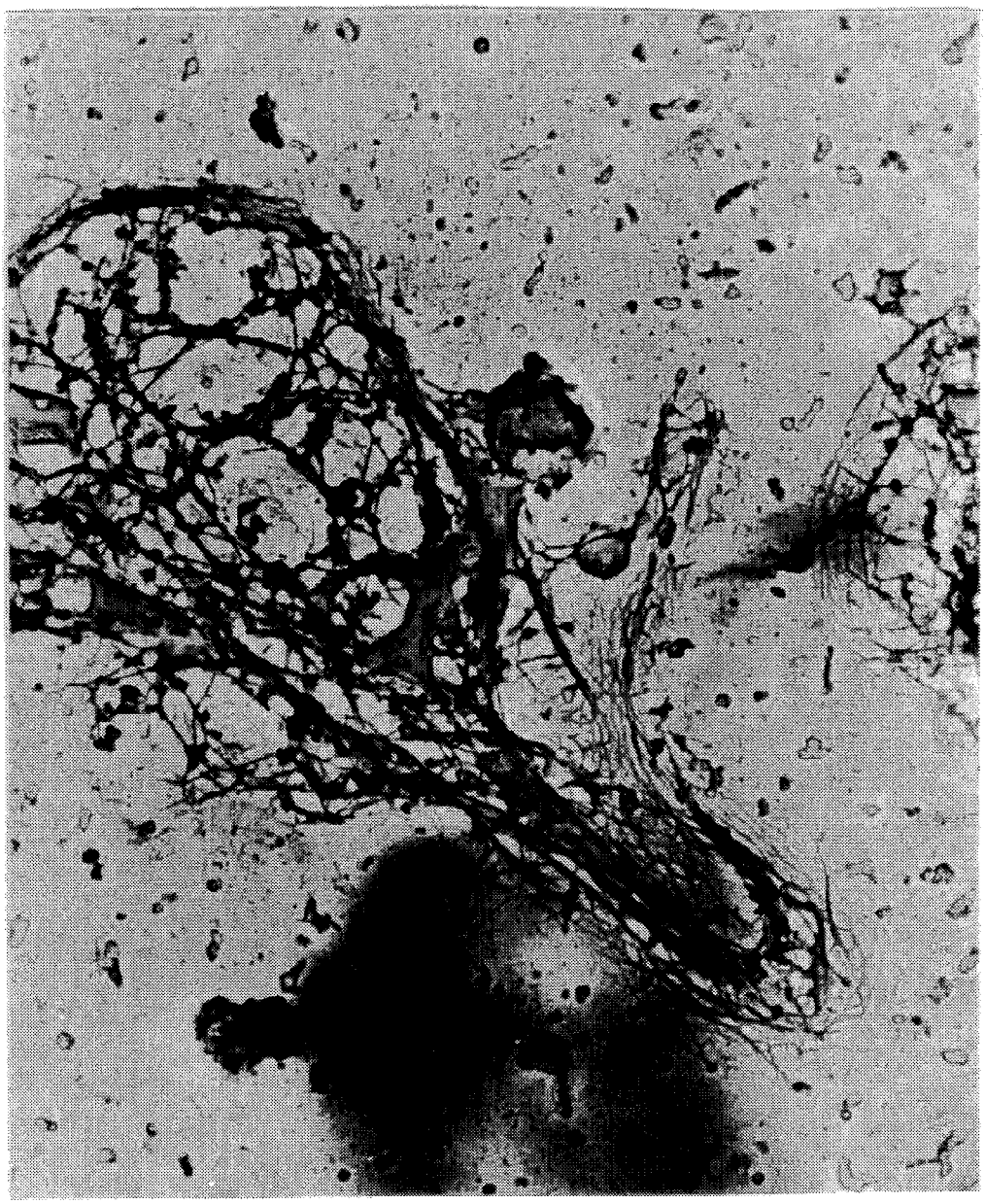
FIG. 10 is a copy of an electron micrograph of a detergent-extracted cold-exposed platelet which was rapidly frozen, metal-shadowed and photographed at about 40,000× magnification.

FIG. 10 is a copy of an electron micrograph of a detergent-extracted, cold-exposed platelet which was rapidly frozen, metal-shadowed and photographed at about 40,000× magnification. FIG. 10 illustrates the bulbous distortion of a cold-exposed platelet by actin filament coils, which distortion resembles that observed for platelets treated with quin-2AM alone (see FIGS. 3 and 7). This result is consistent with the hypothesis that chilling results in the uncapping (presumably ppI-mediated) of gelsolin-ligated actin filament barbed ends in the resting platelets and desequestration of actin monomers. Thus, filament growth, occurring in he absence of severing, results in actin filament coi s which distort the platelet shape.

FIG. 5 illustrates actin polymerization activity in response to cold exposure or thrombin treatment (see Example 3 and Howard, T. H. and Oresajo, J., 1987 supra.). The actin polymerization activity of platelets (never chilled) which were activated by exposure to thrombin (1 U/ml) at 37° C. is shown in FIG. 5, column E and represents the positive control. Actin polymerization induced by chilling alone (4° C.) is shown in column A. Actin polymerization induced by chilling is enhanced for platelets that are chelated (1 uM Quin-2 AM) and cytochalasin-treated (2 uM cytochalasin B) if the cytochalasin is remove in the cold (column B). Chelation and cytochalasin treatment (treated for 30 minutes at 37° C.) completely prevented cold-induced actin assembly so long as cytochalasin was present during the rewarming step (column C), even in the presence of thrombin (1 U/ml) (column D).

The actin polymerazation activity of Quin-2AM-(40 uM) and cytochalasin B- (2 uM) treated platelets (treated for 90 minute at 4° C., see FIG. 5, column F), which were warmed to 37° C., washed (to removed cytochalasin B and to which unchelated calcium (1 mM) was added, approached the actin polymerization activit observed for the positive control. The morphology of the chelated and cytochalasin-treated patelets (FIG. 5, column E) was indistinguishable from platelets that had never been exposed to cold temperatures.

It should be understood that the preceding is merely a detailed description of certain preferred embodiments. It therefore should be apparent to those skilled in the art that various modifications and equivalents can be made without departing from the spirit or scope of the invention.

What is claimed is:

1. A storage composition for preventing cold-induced platelet activation, comprising, plasma containing a plurality of platelets;

a non-naturally occurring first agent for inhibiting actin filament severing; and a non-naturally occurring second agent for inhibiting acting polymerization, wherein the first and second agents are present in the composition in sufficient amounts so as to prevent cold-induced platelet activation and wherein said composition is stored at a temperature of less than about 15° C.

2. A composition as claimed in claim 1, wherein said first agent is an intracellular calcium chelator.

3. A composition as claimed in claim 2, wherein said intracellular calcium chelator is a lipophilic derivative of a calcium chelator selected from the group consisting of quin-1, quin-2, stil-1, stil-2, indo-1, fura-1, fura-2, fura-3, and BAPTA.

4. A composition as claimed in claim 3, wherein said intracellular calcium chelator is a lipophilic derivative of quin-2.

5. A composition as claimed in claim 1, wherein said second agent is selected from the group consisting of cytochalasin B, dihydro-cytochalasin B and cytochalasin D.

6. A composition as claimed in claim 5, wherein said second agent is cytochalasin B.

7. A storage composition for preventing cold-induced platelet activation, comprising, plasma containing a plurality of platelets;

a first agent for inhibiting actin filament severing; and a second agent for inhibiting actin polymerization, wherein said first and second agents are present in said platelets at concentrations which exceed the concentrations at which the first and second agents are present in naturally occurring platelets and wherein said composition is stored at a temperature of less than about 15° C.

* * * * *